US011766172B2

(12) United States Patent
Rege et al.

(10) Patent No.: US 11,766,172 B2
(45) Date of Patent: Sep. 26, 2023

(54) OPHTHALMIC EXAMINATION AND DISEASE MANAGEMENT WITH MULTIPLE ILLUMINATION MODALITIES

(71) Applicant: Vasoptic Medical Inc., Baltimore, MD (US)

(72) Inventors: Abhishek Rege, Baltimore, MD (US); M. Jason Brooke, University Park, MD (US)

(73) Assignee: Vasoptic Medical Inc., Columbia, MD (US)

( * ) Notice: Subject to any disclaimer, the term of this patent is extended or adjusted under 35 U.S.C. 154(b) by 24 days.

(21) Appl. No.: 16/938,492

(22) Filed: Jul. 24, 2020

(65) Prior Publication Data

US 2021/0015364 A1 Jan. 21, 2021

Related U.S. Application Data

(63) Continuation of application No. 15/295,887, filed on Oct. 17, 2016, now Pat. No. 10,722,116, which is a
(Continued)

(51) Int. Cl.
*A61B 3/14* (2006.01)
*A61B 3/00* (2006.01)
(Continued)

(52) U.S. Cl.
CPC .............. *A61B 3/14* (2013.01); *A61B 3/0008* (2013.01); *A61B 3/0025* (2013.01);
(Continued)

(58) Field of Classification Search
CPC .......... A61B 2560/0475; A61B 5/6803; A61B 5/02007; A61B 5/0013; A61B 3/18;
(Continued)

(56) References Cited

U.S. PATENT DOCUMENTS 4,743,107 A * 5/1988 Aizu .................... A61B 3/1225
356/28.5
5,058,596 A 10/1991 Makino et al.
(Continued)

FOREIGN PATENT DOCUMENTS

CN 102596019 A 7/2012
EP 0234869 A2 * 2/1987
(Continued)

OTHER PUBLICATIONS

First Office Action issued in Chinese Patent Application No. 201910550430.3 dated Apr. 14, 2021, and English translation thereof, 24 pages.
(Continued)

*Primary Examiner* — James R Greece
(74) *Attorney, Agent, or Firm* — Pierce Atwood LLP

(57) ABSTRACT

Imaging various regions of the eye is important for both clinical diagnostic and treatment purposes as well as for scientific research. Diagnosis of a number of clinical conditions relies on imaging of the various tissues of the eye. The subject technology describes a method and apparatus for imaging of the back and/or front of the eye using multiple illumination modalities, which permits the collection of one or more of reflectance, spectroscopic, fluorescence, and laser speckle contrast images.

18 Claims, 15 Drawing Sheets

Related U.S. Application Data continuation of application No. 14/855,329, filed on Sep. 15, 2015, now Pat. No. 9,492,083, which is a continuation of application No. PCT/US2014/025014, filed on Mar. 12, 2014.

(60) Provisional application No. 61/788,835, filed on Mar. 15, 2013.

(51) Int. Cl.
| | |
|---|---|
| *A61B 3/12* | (2006.01) |
| *A61B 3/15* | (2006.01) |
| *A61B 5/00* | (2006.01) |
| *A61B 5/02* | (2006.01) |
| *G02B 27/48* | (2006.01) |
| *A61B 3/18* | (2006.01) |

(52) U.S. Cl.
CPC .......... *A61B 3/0033* (2013.01); *A61B 3/0041* (2013.01); *A61B 3/0075* (2013.01); *A61B 3/0083* (2013.01); *A61B 3/0091* (2013.01); *A61B 3/12* (2013.01); *A61B 3/1208* (2013.01); *A61B 3/1233* (2013.01); *A61B 3/1241* (2013.01); *A61B 3/152* (2013.01); *A61B 3/18* (2013.01); *A61B 5/0013* (2013.01); *A61B 5/02007* (2013.01); *A61B 5/6803* (2013.01); *G02B 27/48* (2013.01); *A61B 2560/0475* (2013.01)

(58) Field of Classification Search
CPC ..... A61B 3/1233; A61B 3/1241; A61B 3/152; A61B 3/1208; A61B 3/12; A61B 3/0091; A61B 3/0083; A61B 3/0075; A61B 3/0041; A61B 3/0033; A61B 3/0025; A61B 3/0008; A61B 3/14; G02B 27/48
USPC .......................................... 351/205, 206, 246
See application file for complete search history.

(56) References Cited

U.S. PATENT DOCUMENTS

| | | | |
|---|---|---|---|
| 5,090,799 | A | 2/1992 | Makino et al. |
| 5,129,400 | A | 7/1992 | Makino et al. |
| 5,479,926 | A | 1/1996 | Ustuner et al. |
| 5,583,795 | A | 12/1996 | Smyth |
| 8,596,786 | B2 * | 12/2013 | Bublitz ................ A61B 3/113 351/209 |
| 2003/0112410 | A1 | 6/2003 | Altmann |
| 2003/0231285 | A1 | 12/2003 | Ferguson |
| 2008/0100612 | A1 | 5/2008 | Dastmalchi et al. |
| 2008/0111970 | A1 | 5/2008 | Kakuuchi et al. |
| 2008/0111971 | A1 * | 5/2008 | Gerlitz ............... A61B 5/14532 351/221 |
| 2012/0162438 | A1 | 6/2012 | Thakor et al. |
| 2012/0203086 | A1 | 8/2012 | Rorabaugh et al. |
| 2012/0257164 | A1 * | 10/2012 | Zee ........................ A61B 3/12 351/246 |

FOREIGN PATENT DOCUMENTS

| | | |
|---|---|---|
| WO | 2011029086 A2 | 3/2011 |
| WO | 2013049123 A1 | 4/2013 |

OTHER PUBLICATIONS

International Search Report dated Jul. 18, 2014 from corresponding PCT Application No. PCT/US2014/025014.
Abhishek Rege et al., "Anisotropic Processing of Laser Speckle Images Improves Spatiotemporal Resolution," IEEE Transactions on Biomedical Engineering, vol. 59, No. 5, May 2012, pp. 1272-1280.
Kartikeya Murari et al., "Contrast-enhanced imaging of cerebral vasculature with laser speckle," Applied Optics, vol. 46, No. 22, Aug. 1, 2007, pp. 5340-5346.
Abhishek Rege et al., "Multiexposure laser speckle contrast imaging of the angiogenic microenvironment," Journal of Biomedical Optics, vol. 16, No. 5, May 2011, pp. 056006-1-056006-10.
Abhishek Rege et al., "Imaging Microvascular Flow Characteristics Using Laser Speckle Contrast Imaging," Proc 32nd Ann Intl Conf IEEE Engr Med Biol Soc (EMBC), Buenos Aires, pp. 1978-1981.
Abhishek Rege et al., "Longitudinal in vivo monitoring of rodent glioma models through thinned skull using laser speckle contrast imaging," Journal of Biomedical Optics, vol. 17, No. 12, Dec. 2012, pp. 126017-1-126017-10.
Nan Li et al., "High spatiotemporal resolution imaging of the neurovascular response to electrical stimulation of rat peripheral trigeminal nerve as revealed by in vivo temporal laser speckle contrast," Journal of Neuroscience Methods, vol. 176, 2009, pp. 230-236.
Peng Miao, "High Resolution Cerebral Blood Flow Imaging by Registered Laser Speckle Contrast Analysis," IEEE Transactions On Biomedical Engineering, vol. 57, No. 5, May 2010, pp. 1152-1157.
Office Action dated Sep. 4, 2018 in Chinese Patent Application No. 201480028100.3, and English translation thereof (16 pages).

* cited by examiner

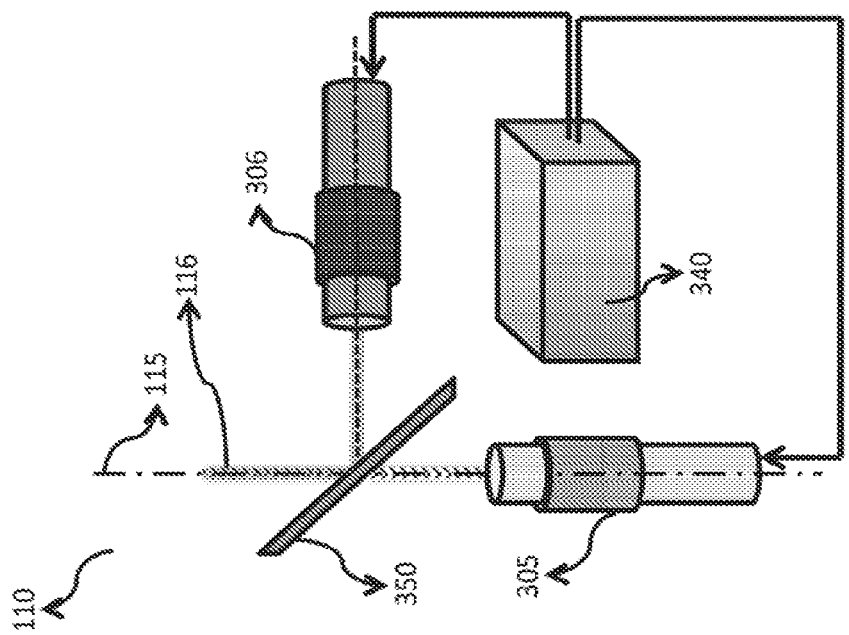
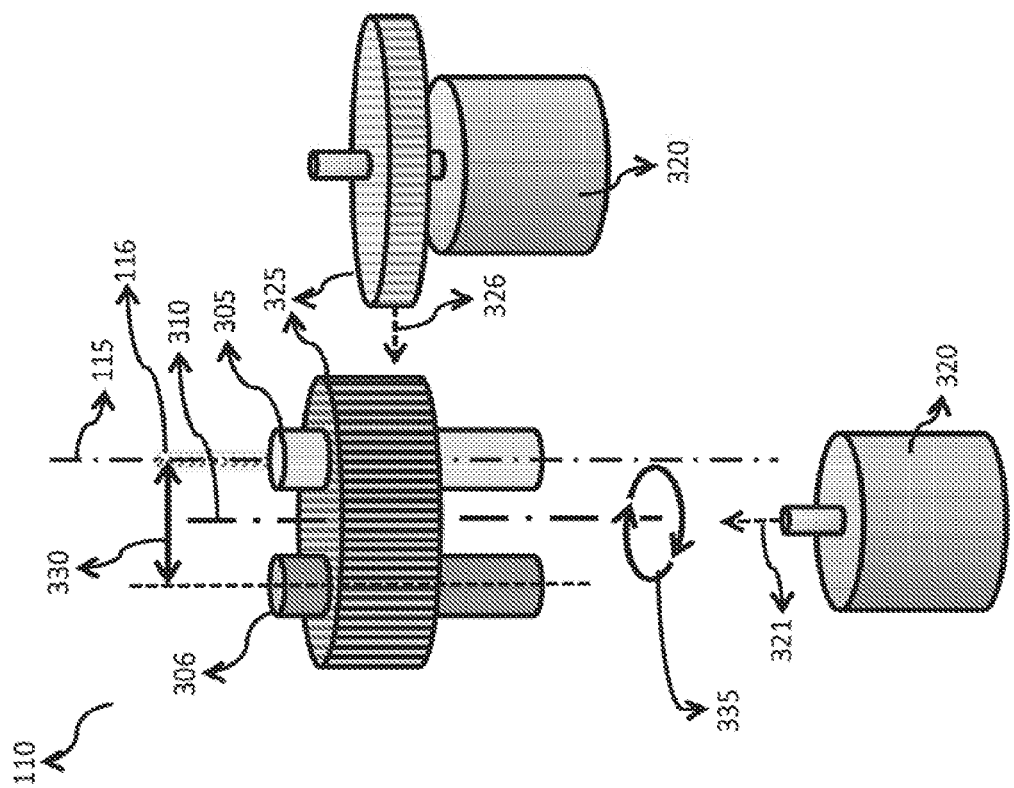

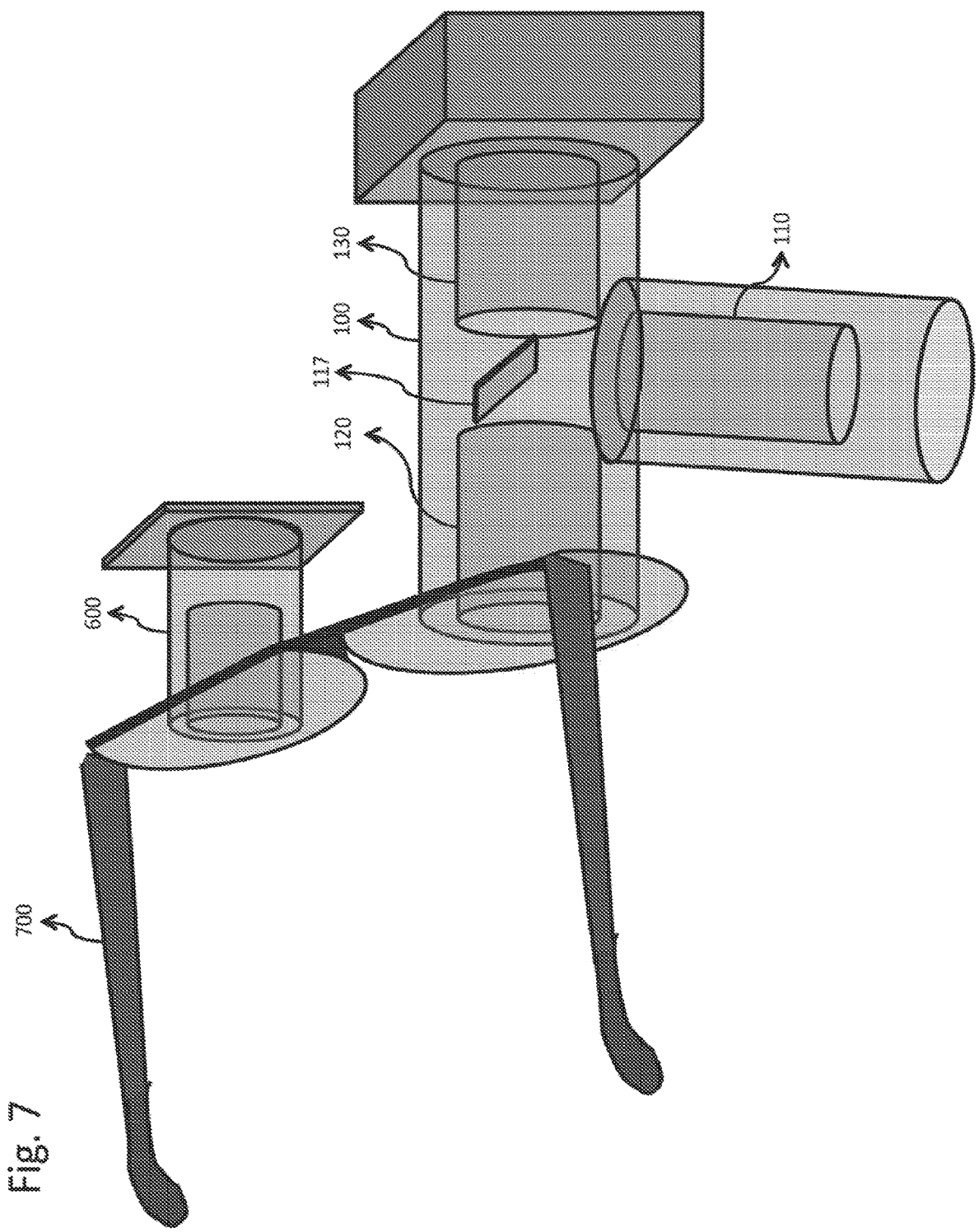

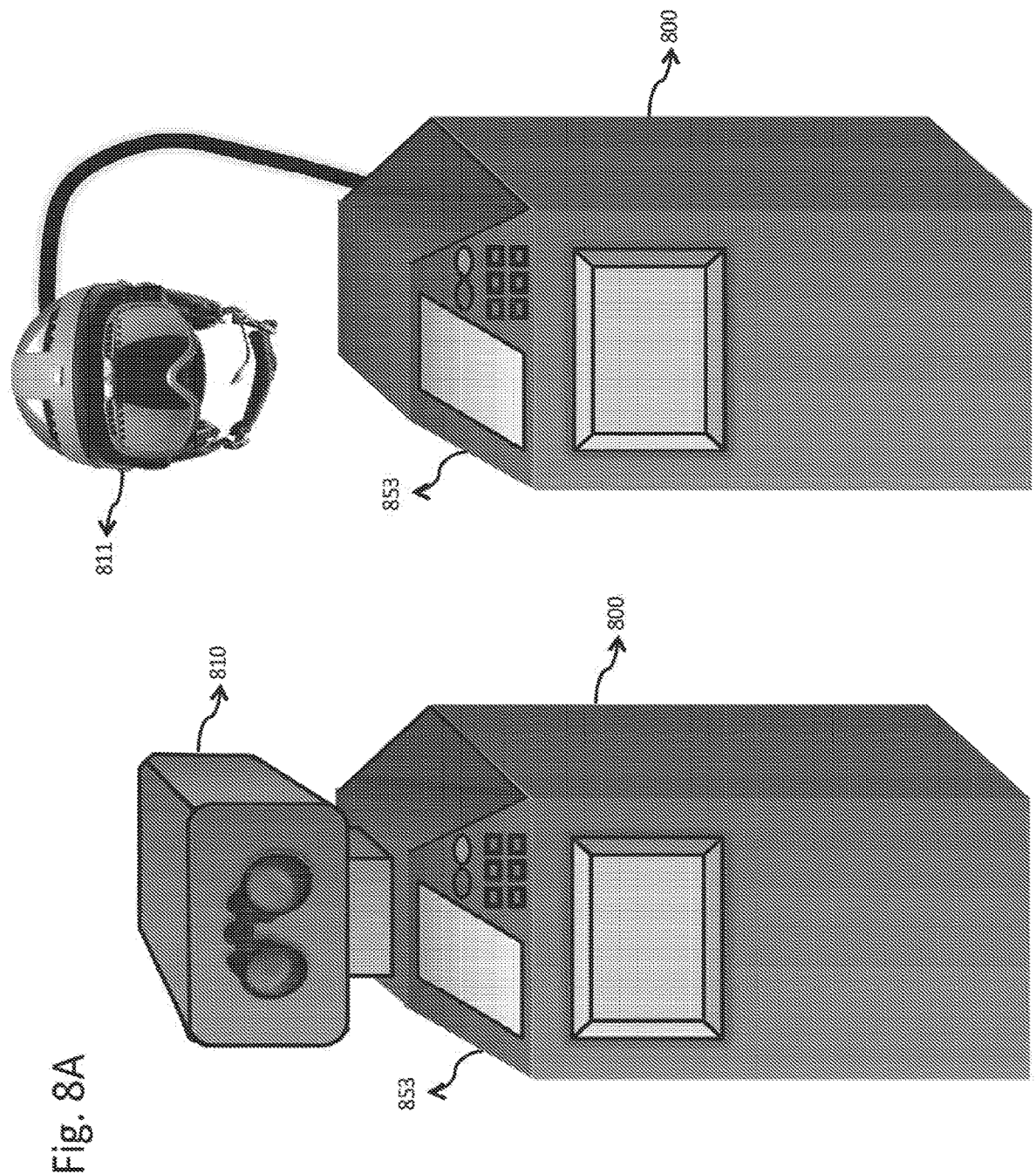

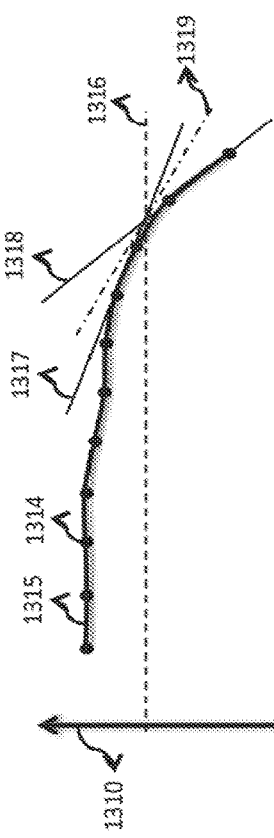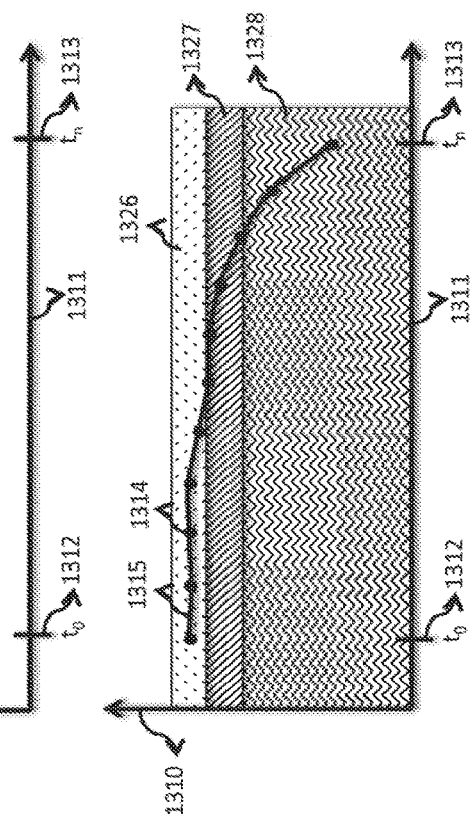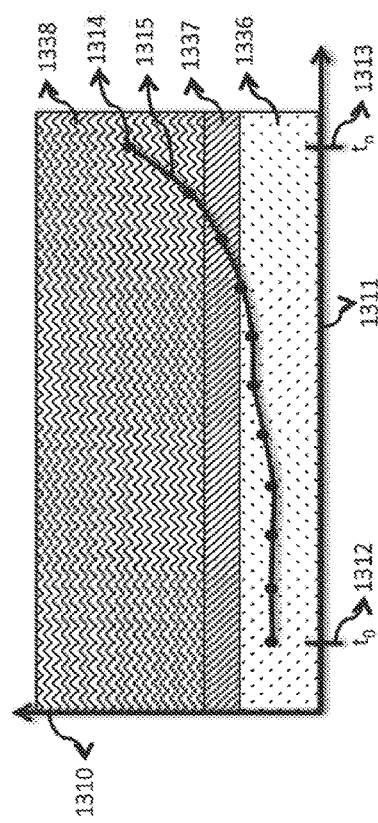

OPHTHALMIC EXAMINATION AND DISEASE MANAGEMENT WITH MULTIPLE ILLUMINATION MODALITIES

RELATED APPLICATIONS

This application is a continuation of U.S. patent application Ser. No. 15/295,887, filed Oct. 17, 2016, which is a continuation of U.S. patent application Ser. No. 14/855,329, filed Sep. 15, 2015, now U.S. Pat. No. 9,492,083, which is a continuation of International Application No. PCT/US2014/025014, filed Mar. 12, 2014, which claims the benefit of U.S. Provisional Application No. 61/788,835, filed Mar. 15, 2013, the entirety of which is incorporated herein by reference.

GOVERNMENT LICENSE RIGHTS

This invention utilized government support under grant 1R43EY023018-01 awarded by the National Eye Institute (of the National Institutes of Health). The government has certain rights in the invention.

FIELD

The subject technology relates to imaging regions of tissue. In particular, the subject technology relates to clinical diagnostic and treatment modalities, ophthalmic examination, and disease management.

BACKGROUND

Imaging the internal regions of the eye is important for both clinical diagnostic and treatment purposes as well as for scientific research. Diagnosis of a number of clinical conditions (e.g., diabetic retinopathy (DR), hypertensive retinopathy (HR), age related macular degeneration (AMD), retinopathy of prematurity (ROP), retinal detachment, glaucoma, cataract, and various types of neovascularization pathologies in the choroid (CNV), cornea and retina) relies on imaging appropriately the retina, choroid, the cornea, the sclera, or the eye lens, including imaging specific aspects of each of these tissues (e.g., blood, blood vessels, exudates, and other anatomical and physiological features). A number of these pathophysiologies are gradual—that is, these disorders develop over time-making a strong case for timely diagnosis and management. For example, unmanaged diabetes and DR leads to proliferation of blood vessels in the retina, blood leakage into the eye and eventually, loss of vision. Thus, not only does retinal imaging have a role in detecting the evidence of a pathophysiology, but also in diagnosing its severity. Early diagnosis through routine monitoring is important in disease management and so, eye screening is becoming an increasingly important aspect in primary care.

In addition to these ophthalmic diseases, imaging of the blood vessels of ophthalmic tissue can be used to detect non-ophthalmic diseases or conditions. These non-ophthalmic disease or conditions can be organ-specific or systemic. For example, reports in literature have also indicated that early signs of brain disorders are also manifested in the retina. Thus, imaging the retina can be used for early diagnosis or risk assessment of conditions like stroke and other types of brain lesions. Similarly, systemic disease (e.g., heart disease or diabetes) can be diagnosed and monitored based on an evaluation of the retinal blood vessels.

SUMMARY

The subject technology describes a method and apparatus for imaging of the back (i.e., the retina and/or the choroid) and/or front (i.e., the cornea and the sclera) of the eye using multiple illumination modalities. The use of multiple illumination modalities allows for imaging under, for example, coherent and incoherent illumination, the timing of which can be controlled for the desired imaging technique. Coherent illumination means the degree of coherence of the emitted optical beam is high (e.g., green, red, blue, or near infrared laser) and includes, among other things, diode lasers and vertical cavity surface emitting lasers (VCSEL). Incoherent illumination means the degree of coherence of the emitted optical beam is low (e.g., white or spectrally filtered light from a light emitting diode (LED) or a halogen lamp). Use of multiple illumination modalities permits the ophthalmic imaging device (called "OID" hereafter) to capture one or more of reflectance images, absorption spectroscopic images, fluorescence images, and LSCI images with or without mydriatic agents.

The OID can be used both in the clinic and the laboratory to image the tissue of the eye of humans and animals to provide quantitative anatomical and physiological information for assessment of tissue function and management of correlated diseases. Imaging of the tissue of the eye includes, for example, the imaging of anatomical features of the retina (e.g., the location, length, density, and type of blood vessels) and associated physiological parameters (e.g., blood flow rates, oxygenation, hematocrit, and changes in diameter, length, density, oxygenation, and hematocrit) that indicate retinal function. The OID can also image blood, as in the case of hemorrhages and blood leakage resulting from blood vessel proliferation and damage. Thus, the OID can be used to monitor the retinal anatomy and physiology for research and diagnosis of a number of pathophysiologies (e.g., DR, HR, ROP, AMD, and retinal detachment). Similarly, the OID can be used to image the choroid, the cornea, and the sclera to detect or evaluate diseases of these tissues (e.g., choroidal neovascularization). The OID can be designed either as different embodiments that are customized for the application but employ the principles disclosed herein, or as a single embodiment that contains adjustable components providing for use in both humans and animals.

The OID can also be utilized to monitor efficacy of medical interventions in the eye during and after the procedure. Such interventions might be surgical (e.g., laser photocoagulation surgery or keratoplasty) or chemotherapeutic (e.g., use of an anti-VEGF drug in the eye or investigation of eye drops). The OID can be used as a real-time or near-real-time feedback mechanism during, for example, any surgical procedure where monitoring of vascular changes would be of relevance. To illustrate this example, the OID can present the real-time LSCI images and blood flow parameters in front of the surgeon's eye using a display mechanism built into a glasses-like device worn by the surgeon or using some physical or virtual screen viewable by the surgeon. The OID can be used as a therapy-planning tool (i.e., to guide medical interventions). For example, the OID can identify specific blood vessels that are candidates for laser photocoagulation surgery in the eye and this information can be presented to the surgeon for consideration. The OID can be used as a therapy control mechanism to automatically control, for example, a computer-guided laser for blood vessel photocoagulation or to trigger the delivery or prescription of a specific medication. The OID can also be used for therapy-planning in a manner that allows the therapy to avoid certain types of blood vessels.

The OID can be used to detect non-ophthalmic diseases or conditions. These diseases or conditions can be organ-specific or systemic. For example, the OID can be used for early diagnosis or risk assessment of conditions like stroke and other types of brain lesions. Similarly, systemic disease (e.g., heart disease or diabetes) can be diagnosed and monitored based on an evaluation of the anatomical and physiological information obtained with the OID (e.g., changes in retinal blood flow rates).

Finally, the OID can be incorporated into an electronic health records (EHR) system or a mobile disease management system as a feedback mechanism to improve diagnosis or treatment of the specific disease target. For example, the OID can automatically store the images obtained into the patient's EHR for subsequent viewing and analysis. In addition, the OID can automatically make notations in the EHR indicating a number of important health information (e.g., the date of the most recent eye exam, the risk level for a specific disease, and the specific values of physiological parameters indicative of the disease). The OID can also produce a report of this information that can be incorporated into an EHR or other similar system and/or transmitted to an appropriate healthcare provider, caregiver, or the patient.

An example of incorporating the OID into a mobile disease management system is for early diagnosis and associated management of DR, a complication of diabetes with symptoms in the eye. Diabetes and its progression could be tracked through routine monitoring of the eye using the OID and subsequent incorporation of the data into an EHR report. Such data can be stored in a time-stamped manner, and blood vessel information (e.g., vessel diameter and blood flow) could be compared through graphs, image overlays, difference images, and other visualization methods. Such data (and associated comparative analyses) could be made available to physicians and specialists for a more detailed understanding of the history and current state of the disease, so that custom care can be provided.

According to some embodiments, an ophthalmic imaging device includes: A) an illumination module capable of generating a plurality of illumination modalities, wherein the illumination modalities include coherent illumination and incoherent illumination, and wherein the illumination module can be configured to perform one or more of laser speckle contrast imaging, spectroscopic imaging, reflectance imaging, or fluorescence imaging; B) one or more imaging sensors configured to collect light from the one or more regions of tissue of the eye; C) an optical assembly including one or more optical elements configured to direct light from the illumination module to one or more regions of tissue of the eye, and further configured to direct light from the one or more regions of tissue of the eye to the one or more imaging sensors; or a first optical assembly including one or more first optical elements configured to direct light from the illumination module to one or more regions of tissue of the eye and a second optical assembly including one or more second optical elements configured to direct light from the one or more regions of tissue of the eye to the one or more imaging sensors; wherein the one or more regions of the tissue of the eye include the retina, choroid, the cornea, the sclera, and the eye lens.

According to some embodiments, the one or more optical elements, the one or more first optical elements, and/or the one or more second optical elements can be an aperture that results in the production of a speckle pattern on the one or more imaging sensors. The ophthalmic imaging device can further include one or more processors configured to control the arrangement of the one or more optical elements, to control durations, duty cycles, and synchrony of the plurality of illumination modalities and the one or more imaging sensors, to control one or more image acquisition parameters, or to process data generated from the one or more imaging sensors to perform one or more of laser speckle contrast imaging, spectroscopic imaging, reflectance imaging, and fluorescence imaging. The one or more optical elements of the optical assembly can be configured to direct light to the one or more regions of tissue of the eye can include one or more spectrally selective filters configured to restrict the illumination from the one or more sources of incoherent illumination to one or more narrow bands of light, wherein the narrow bands of light include green light, blue light, red light, and near infrared light. The ophthalmic imaging device can further include one or more neutral density filters configured to attenuate the illumination power of the one or more sources of coherent or incoherent illumination. The ophthalmic imaging device can further include one or more filters configured to reject harmful wavelengths for a specific application. The light directed to the one or more regions of tissue of the eye can include one or more illumination beams generated from the illumination module. The one or more illumination beams can be coaxial with the optical axis of the imaging path. The one or more illumination beams can be not coaxial with the optical axis of the imaging path. The light directed to the one or more regions of tissue of the eye from the one or more illumination beams can occur synchronously or asynchronously.

According to some embodiments, the ophthalmic imaging device can further include one or more kinematic elements for engaging, indexing, or linear translation of the one or more optical elements, wherein the one or more kinematic elements includes stepper motors, rotors, gears, and guide rails. The ophthalmic imaging device can further include one or more means of user input, wherein the one or more means of user input includes one or more buttons, switches, touchscreens, physical or virtual keyboards, or means to control a cursor. The ophthalmic imaging device can further include one or more means of data transmission to uni-directionally or bi-directionally exchange information with one or more storage devices, display devices, or processing devices, wherein the one or more storage devices, display devices, or processing devices can be standalone or associated with one or more remote computers or servers. The one or more processors can be further configured to calculate laser speckle contrast values for pixels of the one or more imaging sensors associated with the one or more regions of tissue of the eye, wherein the calculated laser speckle contrast values use properties of a pixel's neighborhood of pixels in spatial or temporal domains. The one or more processors can be further configured to extract information from data received, wherein the extracted information includes estimates of blood velocity, estimates of blood flow, blood vessel diameters, spatial density of blood vessels, or classification of blood vessels as arterioles or venules. The one or more processors can be further configured to acquire an image stack and to register images of the acquired image stack to a reference image, wherein the reference image can be acquired independently or can be one of the images in the acquired image stack.

According to some embodiments, the ophthalmic imaging device can further include a gaze fixation mechanism to facilitate fixation of the eye's gaze on a specified physical or virtual target using the contralateral, non-imaged eye. The gaze fixation mechanism can include an optical assembly consisting of one or more optical elements, wherein the one or more optical elements include lenses, filters, mirrors, collimators, beam splitters, fiber optics, light sensors, and apertures. The gaze fixation mechanism can include one or more kinematic elements to adjust one or more optical elements. The gaze fixation mechanism projects an image of a physical or virtual object at a specified target location with respect to the imaged eye or the contralateral eye, wherein the projected image can be determined prior to or at the time of imaging and the projected image location varies during the course of imaging to facilitate acquisition of images of different regions of the eye. The gaze fixation mechanism can further include a display unit that generates one or more virtual objects, the projected images of which coincide with the intended target for gaze fixation. The gaze fixation mechanism can further include a processing element to control operation of the gaze fixation mechanism and to perform one or more calculations for the operation of the gaze fixation mechanism, wherein the one or more calculations include calculations pertaining to location identification of the intended target of gaze fixation and location identification of the virtual or physical object.

According to some embodiments, the ophthalmic imaging device can further include an immobilization mechanism for stabilization with respect to the subject's eye, wherein the immobilization mechanism can include one or more optical elements and one or more rigid components, wherein the one or more optical elements includes lenses, filters, mirrors, collimators, beam splitters, fiber optics, light sensors, and apertures and the one or more rigid components includes a helmet or one or more nose bridges, sunglasses, goggles, rubber cups, helmets. The disease management system, can further include: A) one or more ophthalmic imaging devices configured to perform one or more of laser speckle contrast imaging, spectroscopic imaging, reflectance imaging, and fluorescence imaging of one or more regions of tissue of the eye, wherein the one or more regions of the tissue of the eye include the retina, choroid, the cornea, the sclera, and the eye lens; one or more sensors configured to collect at least one type of patient-specific data. The disease management system can further include: one or more processors configured to process the anatomical or physiological information from the one or more regions of tissue of the eye and the at least one type of patient-specific data; and one or more interface devices configured to display the at least one type of patient-specific data and to allow the user to input information to change the functionality of the one or more processors. The one or more ophthalmic imaging devices can be configured for one or more diagnostic, prognostic, or therapeutic purposes, wherein the one or more diagnostic, prognostic, or therapeutic purposes include ophthalmic and non-ophthalmic diseases or conditions. The one or more sensors consists of ophthalmic or non-ophthalmic sensors. The processor can be configured to read and analyze the at least one type of patient-specific data from one or more points in time, wherein the analysis includes comparing the at least one type of patient-specific data to one or more thresholds, comparing the at least one type of patient-specific data at different points in time, calculating trends of the at least one type of patient-specific data, comparing trends of the at least one type of patient-specific data to one or more thresholds, extrapolating trends of the at least one type of patient-specific data to estimate the expected future values of the at least one type of patient specific-data, and computing one or more threshold criteria based on population-based statistics associated with the one or more patient-specific data. The one or more thresholds include one or more constant values or values that depend on the attributes of the at least one type of patient-specific data, or values that depend on population-based statistics associated with the at least one type of patient-specific data. The at least one type of patient-specific data includes one or more electrocardiograms, blood pressure measurements, heart rate measurements, pulse oximetry measurements, blood glucose measurements, hemoglobin A1c measurements, ocular pressure measurements, respiratory measurements, plethysmograms, weight measurements, height measurements, age, body position, electroencephalograms, electrooculograms, electroretinograms, visual evoked responses, prior medical history, and information derivative to the at least one type of patient-specific data. The processor can be configured to: trigger one or more types of therapy through one or more manual, semi-automatic, or automatic means; and facilitate the communication of the at least one type of patient-specific data to one or more devices for storage, display, or analysis.

According to some embodiments, a method of imaging a region of tissue of the eye, includes: configuring the ophthalmic imaging device for image acquisition suitable to achieve the desired imaging modality, wherein the configuring step includes maintaining a pre-configured state, adjusting one or more optical assemblies, illumination modalities, and image acquisition parameters; initiating illumination generated by the ophthalmic imaging device; initiating image acquisition based on the image acquisition parameters; storing the acquired images; processing the acquired images; and changing manually or through the configured processing element of the ophthalmic imaging device, the source of coherent incoherent illumination and repeating one or more of the adjusting the optical assembly, setting values for image acquisition parameters, initiating illumination, initiating image acquisition, storing, or processing steps.

According to some embodiments, the method can further include immobilizing an ophthalmic imaging device with respect to a subject's eye. The method can further include instructing the subject to fixate the gaze of the eye on a physical or virtual object. The ophthalmic imaging device can be configured to acquire images using a plurality of imaging modalities, wherein the plurality of imaging modalities includes laser speckle contrast imaging, spectroscopic imaging, reflectance imaging, and fluorescence imaging. The ophthalmic imaging device can be handheld and immobilized by resting or pressing against the subject's face or eye. The ophthalmic imaging device can be used in conjunction with eyeglasses, goggles, a helmet, or other accessory to immobilize the ophthalmic imaging device with respect to the subject's head or eye. The ophthalmic imaging device can be used in conjunction with a chin rest or other accessory to immobilize the subject's head or eye. The virtual object can be generated by the ophthalmic imaging device and the location of the virtual object can be predetermined or determined dynamically by an operator. The optical assembly of the ophthalmic imaging device can contain one or more optical elements that can be adjusted manually by the operator, semi-automatically, or automatically by a processor. The image acquisition parameters can include exposure time, gain, pixel sensitivity, number of images, frame rate, timing sequence, pixel resolution, pixel area, and image magnification. The illumination generated by the ophthalmic imaging device can include light from one or more coherent illumination beams and light from one or more incoherent illumination beams. Storing the acquired images can include recording one or more images on a local or remote storage device, wherein the storage device includes any one or more of random access memory, magnetic or solid state hard disk technology, flash disk technology, or optical disk technology. The processing of acquired images can include registration of acquired images, processing for laser speckle contrast imaging, feature extraction using a combination of one or more of laser speckle contrast images, spectroscopic images, reflectance images, and fluorescence images, processing for spectroscopic imaging, and preparing images or processed images for communication, storage, or display.

According to some embodiments, a method of analyzing images obtained using an ophthalmic imaging device includes: selecting the one or more images and parameters to analyze; selecting the one or more processing algorithms to perform; triggering the one or more processing algorithms; and presenting the output of the one or more processing algorithms.

According to some embodiments, the one or more images can be generated from one or more of laser speckle contrast imaging, spectroscopic imaging, reflectance imaging, and fluorescence imaging. The one or more parameters can be one or more of anatomical and physiological parameters extracted from one or more images generated from one or more of laser speckle contrast imaging, spectroscopic imaging, reflectance imaging, and fluorescence imaging. The one or more parameters can be extracted from one or more sensors and includes electrocardiograms, blood pressure measurements, heart rate measurements, pulse oximetry measurements, blood glucose measurements, hemoglobin A1c measurements, ocular pressure measurements, respiratory measurements, plethysmograms, weight measurements, height measurements, age, body position, electroencephalograms, electrooculograms, electroretinograms, visual evoked responses, prior medical history, and information derivative to the one or more parameters. The output can include one or more visual renditions of the one or more images, the one or more parameters, thresholds, trends, and information derivative to the one or more parameters. The method can further include one or more interface devices configured to allow an operator to manipulate one or more of the selecting of the one or more images and parameters to analyze, the selecting of the one or more processing algorithms to perform, the triggering of the one or more processing algorithms, and the presenting of the output of the one or more processing algorithms. The method can further include triggering therapy manually, semi-automatically, or automatically based on the one or more analyzed images or parameters. The therapy includes one or more of a recommendation to the user to change a specific drug medication or to perform some other treatment procedure, a recommendation that allows the user to trigger an automatic treatment or procedure, or an automated signal that controls a treatment mechanism.

According to some embodiments, a method of managing a patient's disease includes: acquiring one or more images of one or more regions of the tissue of the eye using an ophthalmic imaging device; acquiring at least one type of patient-specific data from one or more sensors; processing the one or more images, one or more parameters, and at least one type of patient-specific data; and presenting the processed information for review by a caregiver.

According to some embodiments, the ophthalmic imaging device can be configured to generate the one or more images from one or more of laser speckle contrast imaging, spectroscopic imaging, reflectance imaging, and fluorescence imaging. The method can further include triggering therapy manually, semi-automatically, or automatically based on the one or more processed information.

BRIEF DESCRIPTION OF THE DRAWINGS

FIGS. 3A and 3B are illustrations of various embodiments of the illumination module comprising more than one light source.

FIG. 7 is a schematic of an embodiment for immobilizing the OID with respect to the subject's eye.

FIGS. 8A and 8B illustrate various embodiments for the incorporation of the OID into a standalone system that can be operated by non-experts using a simple interface.

FIGS. 13A, 13B, and 13C illustrate various embodiments for presenting and assessing parameters generated using the OID in accordance with the various embodiments of the subject technology.

DETAILED DESCRIPTION

Figure 1A:
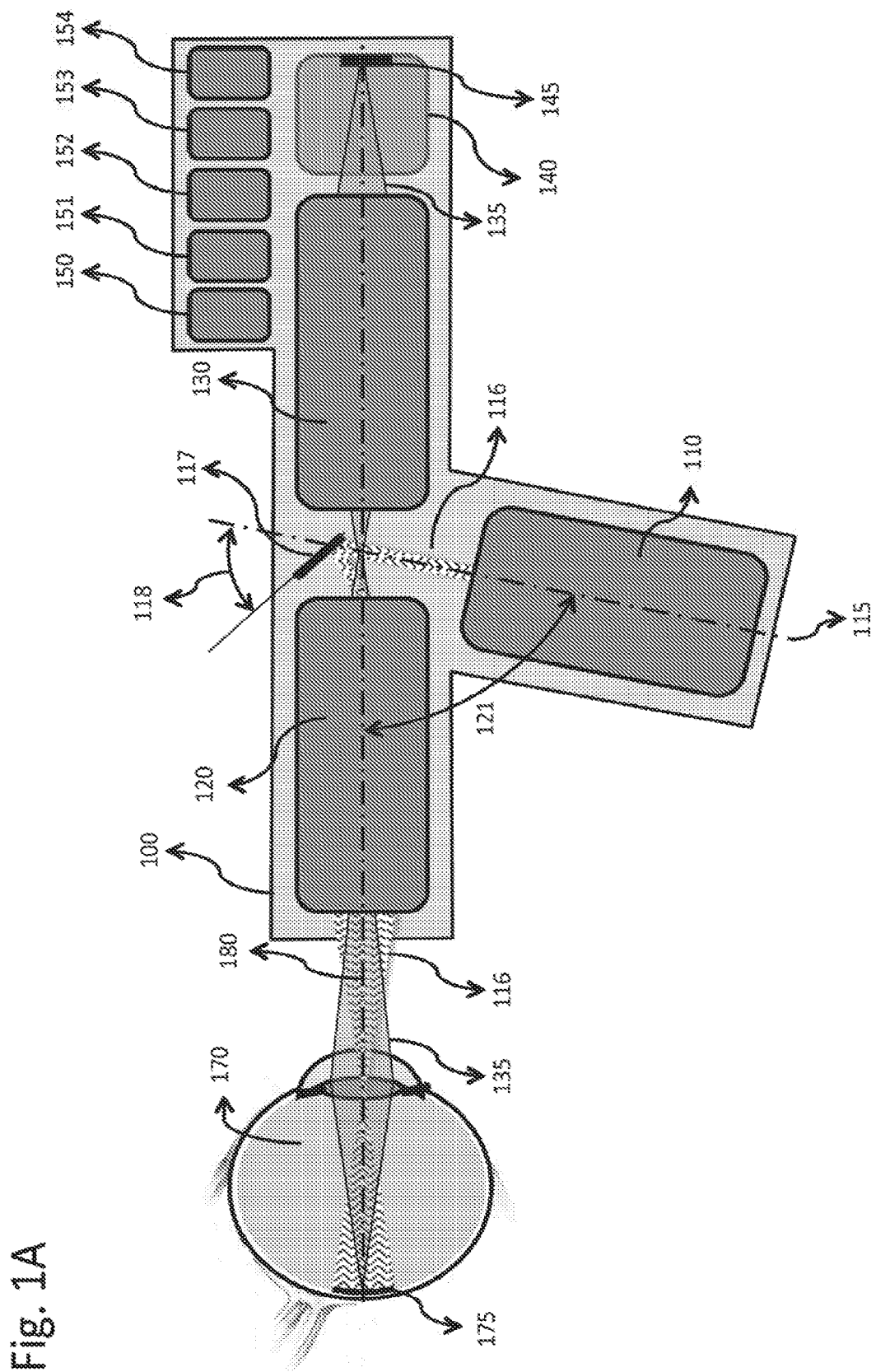
FIG. 1A is a schematic of the OID showing the functional components and optical paths used for acquisition of reflectance, spectroscopic, fluorescence, and laser speckle contrast images of the retinal tissue of the eye.

A number of imaging modalities have been developed that may be of relevance for ophthalmic imaging. These include:

(a) Laser speckle contrast imaging. When images are acquired under coherent (i.e., laser) illumination through an appropriately sized aperture, speckle patterns are formed. The blurring of speckle patterns due to motion can be mathematically estimated using a metric called speckle contrast, defined as the ratio of standard deviation of pixel intensities to the mean value of pixel intensities within a specified neighborhood of every pixel under consideration in the stack of images. The said neighborhood may lie in the spatio-temporal domain, as described in (1).

(b) Spectroscopic imaging. When images acquired under different illumination wavelengths are compared, it is possible to highlight features based on differential absorption, transmission, and reflection of light by different tissue/cell types. For example, differential analysis under near-infrared and green light can distinguish between oxygenated and deoxygenated blood.

(c) Reflectance imaging. This imaging mode is equivalent to photographing the eye under illumination that is similar to ambient light (e.g., light from a flashlight, light from a halogen lamp, etc.). These images also contain information analogous to spectroscopic images, since white light intrinsically contains multiple wavelengths of light. Oxygenated blood (in arteries under normal conditions) appears faint on a grayscale image obtained under white light illumination, while deoxygenated blood (in veins under normal conditions) appear darker.

(d) Fluorescence imaging. If a fluorescent dye is injected in the blood vessels, then high contrast images of blood vessels could be obtained using appropriate illumination wavelengths and optical filters.

Imaging the retina and/or the choroid poses a number of technical and practical challenges:

(a) Given the constraints placed by motion artifact on the camera exposure time in non-stabilized photography, ambient light does not provide adequate illumination for photographing the retina. Very little amount of light is captured by the camera sensor within the small exposure time limiting its ability to achieve high contrast between retinal features. Thus, additional illumination from an external light source is essential.

(b) The geometry of the eye-specifically, the location of the retina, the pupil (and iris), the cornea and lens-does not provide enough leeway for the illumination and imaging paths to be along significantly different directions. This problem has been partially solved in the past using an optical assembly known as a fundus camera. However, the fundus camera cannot perform laser speckle contrast imaging, a method of imaging blood vessels and blood flow.

(c) Incidence of the illuminating light, especially coherent light (i.e., laser) on the retina may be harmful, thus placing a stringent constraint on the amount of energy that can be delivered to the retina to provide illumination for imaging purpose. Conventional retinal imagers that use lasers (e.g., scanning laser ophthalmoscopes) ensure through scanning that the laser illuminates a small region of interest (ROI) for a very short period of time, thus restricting the energy delivered to the retina despite using a beam of high power and intensity. Laser speckle contrast imaging (LSCI) requires simultaneous illumination of the entire field of view (FOV) as opposed to spot illumination and scanning—for longer periods of time in comparison to prior laser-based retinal imaging techniques. The overall illumination time could be as long as 10 seconds. Thus, a low-power laser whose power may be duly attenuated further must be used; and the activation and deactivation of the laser module must be controlled using a mechanical shutter or an electronic switch.

(d) Current retinal imagers place a significant socio-economic burden on its use. The high cost of individual components that make up the retinal imager, makes the overall system expensive. Combining the cost of the device with the additional cost of the eye-care specialists required to perform the procedure drives up the cost of eye exams and overall healthcare expenditures. Further, most retinal imagers require chemically-induced pupil dilation to capture a large FOV, which makes their use complicated and inconvenient.

As described in more detail below, the OID is composed of a plurality of optical elements, illumination modules, cameras, photosensors, power sources, processor elements, storage elements, and communication elements. The specifications and parameters of the imager may change to accommodate differences in the subjects' eyes. For example, rat eyes (used in research) are much smaller in size that human eyes. The rat eye curvature is also different than the curvature of the human eye. Also, the apparatus may be embodied differently for different tissue being imaged. For example, imaging the choroid may require illumination at a higher wavelength than when imaging the retina. Likewise, imaging the cornea may require a different lens assembly than when imaging the retina. The apparatus may also be embodied with adjustable elements that can be moved and/or tuned for specific applications.

Some embodiments incorporate the OID into an external system for disease management and treatment. In some embodiments, the OID communicates with the external system through a wireless connection. In other embodiments, the OID communicates with the external system through a wired connection. In some embodiments, the OID is incorporated into the external system to present data for review and tracking by a healthcare provider. In other embodiments, the OID is incorporated into the external system to recommend specific treatment options. In other embodiments, the OID is incorporated into the external system to automatically control therapy.

FIG. 1A shows an exemplary OID 100 with the functional components and optical paths used for acquisition of images of the target tissue 175 of the back of the human eye 170. Light produced by the illumination module 110 is deflected off the beam deflector 117 and manipulated by Optical Assembly A 120 to illuminate the target tissue 175 (e.g., the patient's retina). This path of light from the illumination module 110 to the target tissue 175 is referred to as the illumination path 116, with the light itself being referred to as the illumination beam. The optical axis of the portion of the illumination path 116 from the illumination module 110 to the beam deflector 117 is called the illumination axis 115. Light reflected from and/or scattered by the target tissue 175 may be manipulated by a combination of Optical Assembly A 120 and Optical Assembly B 130 en route to the image acquisition module 140. This path of light from the target tissue 175 to the image acquisition module 140 is referred to as the imaging path 135 and the optical axis of this path is referred to as the imaging axis 180. The image acquisition module 140 comprises an imaging sensor (e.g., a camera) 145 with the necessary control, processing, and storage elements (e.g., a computer) to acquire, process, and store images of the target tissue 175. The OID 100 can contain a separate processor unit 150 for controlling all or portions of the functional components. Furthermore, the OID 100 contains a power module 154 to provide electrical supply to all or portions of the functional components.

The illumination module 110 can be composed of a plurality of light sources in a plurality of arrangements. The illumination module 110 allows sequential imaging under at least one coherent and at least one incoherent illumination beam. The at least one coherent illumination beam can be generated from green, red, blue, or near infrared laser. The at least one incoherent illumination beam can be generated from white or spectrally filtered light from, for example, an LED or a halogen lamp. The illumination module 110 may be oriented such that the illumination axis 115 is oriented at an angle θ 121 with respect to the imaging axis 180.

The beam deflector 117 can be a mirror or any other reflective object/material oriented at a predetermined angle φ 118 with respect to the illumination axis 115 such that the illumination path 116 can be directed towards the target tissue 175. In other embodiments, angle φ 118 can be determined with respect to the imaging axis 180 instead of the illumination axis 115. In other embodiments, angle φ 118 may be determined based on mechanical elements or casing of the OID 100. The beam deflector 117 is also chosen and located such that it facilitates or does not interfere with the travel of light from the target tissue 175 to the image acquisition sensor 145 along the imaging path 135. In some embodiments, the beam deflector 117 may be located on one side of the imaging axis 180. In some embodiments, the beam deflector 117 may contain a hole for the light reflected from the target tissue 175 to proceed towards the image acquisition module 140. In some embodiments, the beam deflector 117 may be a beam splitter which reflects a portion of the illumination light towards the target tissue 175 while letting the remaining light to pass through. Such a beam splitter will also allow a portion of the light reflected from the target tissue 175 to pass through along the imaging path towards the image acquisition module 140. The ratio of transmitted light and reflected light is a property of the beam splitter and may be anything from 0 to 1. Angle θ 121 may vary from 0° to 180° and angle φ 118 may vary commensurately so as to deflect the illumination path 116 as much along the imaging axis 180 as possible.

Optical Assembly A 120 can be composed of one or more lenses that focus the illuminating light such that the target tissue 175 is illuminated over a large FOV. In some embodiments, the Optical Assembly A 120 can be positioned between the beam deflector 117 and the illumination module 110 such that no lens is necessary in the illumination path 116 from the beam deflector 117 to the target tissue 175. Optical Assembly A 120 can be oriented such that it influences the imaging path 135 and the illumination path 116. In some embodiments, Optical Assembly A 120 is oriented such that it influences only the illumination path 116, that is, light from the illumination module 110 may encounter Optical Assembly A 120 before it encounters the beam deflector 117.

Optical Assembly B 130 comprises a minimum of one lens that focuses the light from the target tissue 175 on the imaging sensor 145 and one aperture that is central to the formation of speckle patterns on the imaging sensor 145. These elements could appear in any order in the imaging path 116. In one embodiment, the order is determined to achieve the dual function of image formation and speckle formation on the imaging sensor. In another embodiment, the lens and aperture arrangement can be replaced by a system of lenses and apertures. Optical Assembly B 130 typically comprises a mechanism to adjust the lens position for appropriate focusing. The mechanism of adjustment can involve movement of one or more lenses and/or apertures along the imaging axis 180. Such movement may be manual, semi-automatic (i.e., motorized but user-triggered and/or controlled) or automatic (i.e., motorized and/or electronically controlled without user intervention). In some embodiments, the adjustment mechanism moves at least 1 cm, though this distance depends on the focal lengths of the lenses used. In some embodiments, alternative adjustment approaches may be employed, including use of a movable camera with a fixed lens system.

The Optical Assembly B 130 is oriented such that it influences only the imaging path 135 and not the illumination path 116. Thus, the objectives of Optical Assembly B 130 are: (a) to form an appropriately sized (i.e., magnified) and appropriately focused image of the target tissue 175 on the imaging sensor 145 or for direct viewing, (b) to achieve a pre-calculated speckle size (i.e., Airy disc diameter) that lies between 5 and 20 micrometers at the imaging sensor 145, and (c) to spectrally filter light en route from the target tissue 175 to the image acquisition module 140 in case fluorescence or spectroscopic imaging is being performed. Accordingly, in one embodiment, Optical Assembly B 130 comprises lens and aperture arrangements that can achieve a 1:1 magnification and a speckle size of approximately 10-12 micrometers. Any magnification between 0.5 and 2.0 and speckle sizes between 5 and 20 micrometers may be acceptable depending on the embodiment and its preferred application.

In some embodiments, particularly those that incorporate fluorescence imaging, Optical Assembly B 130 may include one or more filters. The said filter set can block the illuminating light while letting the fluorescently emitted light to pass through. For example, if fluorescein angiography is being performed, the OID 100 can employ a filter that selectively transmits green (approximately 520 to 540 nm) wavelengths, while blocking all others.

Optical Assembly A 120 and Optical Assembly B 130 are considered separately only for the sake of explanation. In some embodiments, the optical elements of Optical Assembly A 120 and Optical Assembly B 130 may seamlessly substitute the elements of the other. In some embodiments, a lens in Optical Assembly A 120 can be designed (e.g., fusing different lenses together) such that an image can be formed without the need for any subsequent focusing en route to the imaging sensor 145 and, therefore, Optical Assembly B does not require a different lens. Such a lens—ostensibly a single optical element—becomes a functional part of both Optical Assembly A 120 and Optical Assembly B 130.

The image acquisition module 140 comprises at least one imaging sensor 145 that can capture the light coming from the target tissue 175 and store the data in digital form as one or more images. Thus, the at least one imaging sensor 145 includes charge coupled device (CCD) cameras, metal oxide semiconductor (MOS), complementary MOS (CMOS) cameras, photodiodes, phototransistors, and/or photo tubes. Digitization of the light sensor data can be done immediately after sensing, as in most cameras, or an analog-to-digital convertor (ADC) may be used subsequent to an analog camera. The imaging sensor 145 may or may not have an embedded processor as part of the OID 100. In one embodiment, a field programmable gate array (FPGA) or an equivalent programmable unit may process the images acquired and store the image or relay the resulting image for further consideration. In another embodiment, the imaging sensor 145 may store the acquired image(s) on to a memory device (e.g., a flash disk), which then may be used to transfer the data for further processing. In a third embodiment, the imaging sensor 145 may be connected to a processor and storage unit through a communication channel (e.g., the universal serial bus (USB)) and relay the acquired images in real-time or near real-time to a nearby processing unit (e.g., computer or embedded processor). Other communication channels that can achieve a similar function are the IEEE 1394 (fire wire) ports, serial/parallel port, IDE, and/or the serial/parallel ATA. Image transfer may also be performed using wireless modules that utilize one or more of Wi-Fi, 2G, 3G, 4GLTE, Bluetooth, and infrared channels. Transmission of the data may utilize any of the acceptable formats (e.g., DICOM, HL7, or other similar standards) for image transmission and compliant with health data and internet security standards. Data may be processed exclusively for the intention of transmission (e.g., encryption for security, compression for transmission speed, etc.) and commensurately processed again (e.g., decryption, decompression, etc.) at the receiving system for further use, processing or display.

The size and type of the storage element 152 is dependent on the embodiment of the OID 100. For example, the storage element can be large (e.g., 16 to 256 GB) to accommodate local storage for subsequent 1) viewing on a user interface module 153 (e.g., liquid crystal display) built into the OID 100, 2) image analysis, and 3) transmission to an external computing platform (e.g., for remote storage, analysis, or display). Alternatively, the storage element can be small (e.g., 1 to 16 GB) to accommodate temporary local storage for transmission to an external computing platform (e.g., for remote storage, analysis, or display). The storage element could utilize any of random access memory (RAM) technology, magnetic or solid state hard disk technology, flash disk technology, or optical disk technology.

The OID 100 contains a power module 154 that can be a combination of one or more of direct current (DC) sources and alternating current (AC) sources converted through an AC to DC adaptor. For example, one embodiment incorporates use of one or more non-rechargeable batteries that power all electronics within the OID 100. Another embodiment may incorporate one or more rechargeable batteries in conjunction with an AC to DC adaptor. Each electronic element of the OID 100 may draw power from sources independent of other electronic elements. For example, the image acquisition module 140 may draw power from a USB, while the illumination module(s) 110 may use dedicated rechargeable or non-rechargeable batteries.

The beam deflector 117 may lie in the imaging path 135 instead of the illumination path 116. In such an embodiment, the path of light from the illumination module 110 to the target tissue 175 may lie along a single straight line, but the path of light from the target tissue 175 to the imaging acquisition module 140 may involve one or more deflections by appropriately positioned beam deflectors 117. Whether in the illumination path 116 or the imaging path 135, the purpose of the beam deflector 117 is to alter the direction of light leading up to it and orient the light in the desired direction. This function can also be achieved using one or more fiber optic cables and/or optical waveguides. Fiber optic cables are often flexible along their length and thus, relax space and position constraints on the illumination module 110.

Figure 1B:
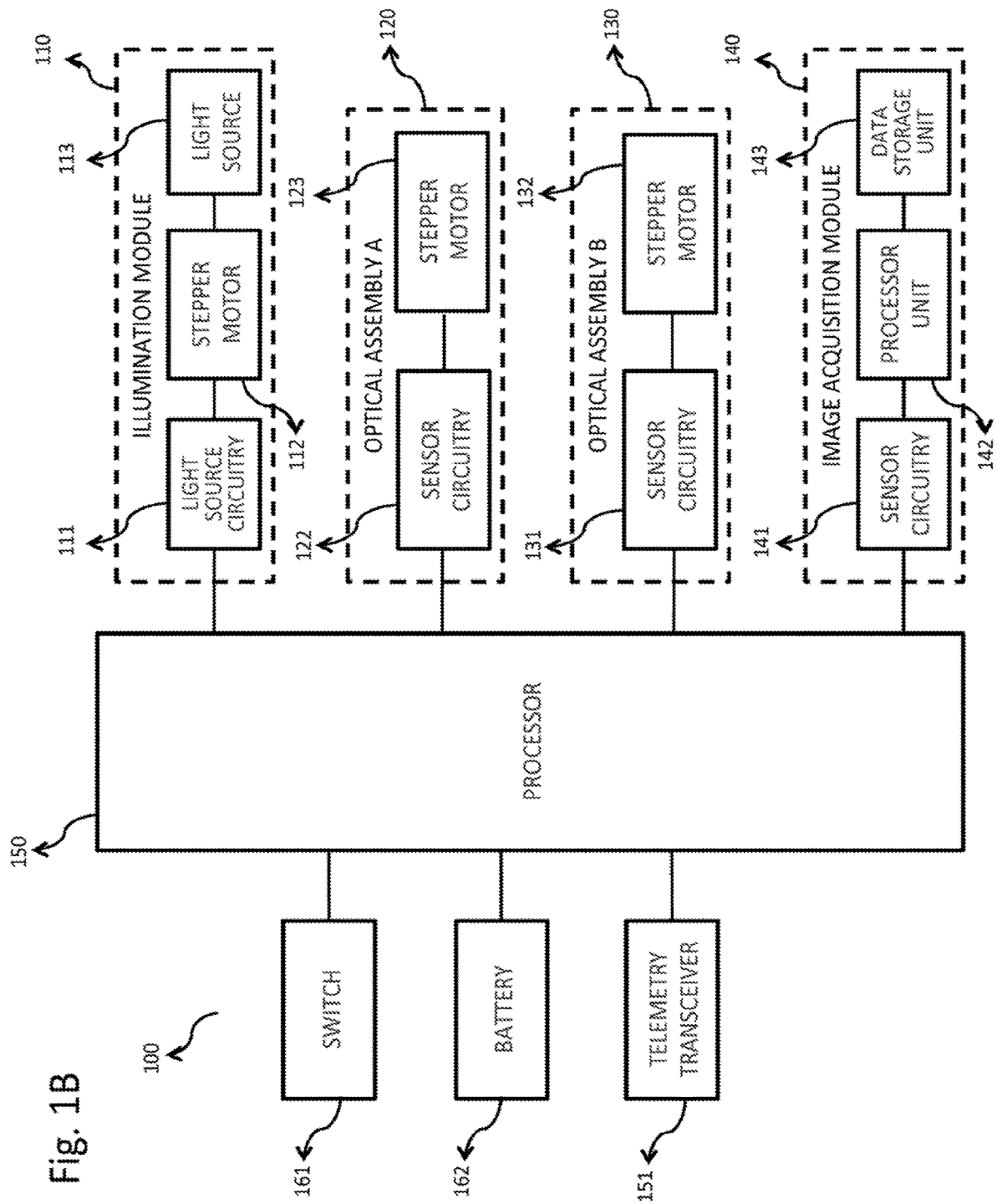
FIG. 1B is a schematic of the electrical components of the OID.

FIG. 1B shows a schematic of the electrical components of an exemplary OID 100. A switch 161 allows the user to activate or deactivate the functionality of the OID 100 while one or more batteries 162 power the electrical components. In some embodiment, the one or more batteries 162 can power some or all of the electrical components of the OID 100. In some embodiments, the one or more batteries 162 may be incorporated within the OID 100, while in other embodiments, one or more of the batteries 162 can be external. A telemetry transceiver 151 allows data to be transmitted to and from the OID 100. In some embodiments, the telemetry transceiver 151 may be replaced by another communication mechanism. A processor unit 150 processes signals from the various electrical components, including the illumination module 110, Optical Assembly A 120 and Optical Assembly B 130, and the image acquisition module 140. The illumination module comprises a light source circuitry unit 111 and a stepper motor unit 112 to manipulate the light source 113. The Optical Assembly A 120 comprises sensor circuitry 122 and a stepper motor unit 123. The Optical Assembly B 130 comprises sensor circuitry 131 and a stepper motor unit 132. The image acquisition module 140 comprises sensor circuitry 141, a processor unit 142, and a data storage unit 143.

The control of the various modules of the OID 100 can be achieved using any processor unit 150. Examples of control activity include: invoking the appropriate illumination module 110 for an appropriate amount of time, motion of the components of the Optical Assembly A 120 and Optical Assembly B 130 for focusing on appropriate ROI of the target tissue 175, control of the gaze fixation apparatus (described below), recording and basic processing of images under appropriate illumination, invoking the appropriate modality for storage and/or transmission of the images, power management, data management and storage, and invoking advanced analytics on the images. One embodiment will have the processor unit 150 physically located on the OID 100 and could be an FPGA, a microprocessor, or a microcontroller. Another embodiment has the processor unit 150 located remotely and communication to and from the OID 100 will be established via a telemetry transceiver 151, USB, or any other standard or proprietary channels.

Figure 2B:
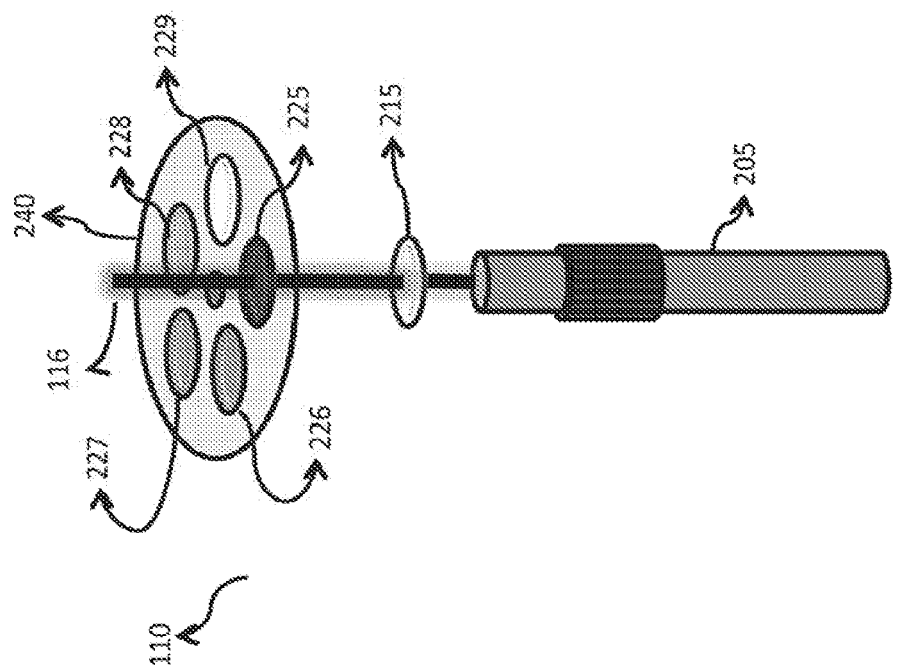
FIGS. 2A and 2B illustrate various embodiments of the illumination module of the OID.
Figure 2A:
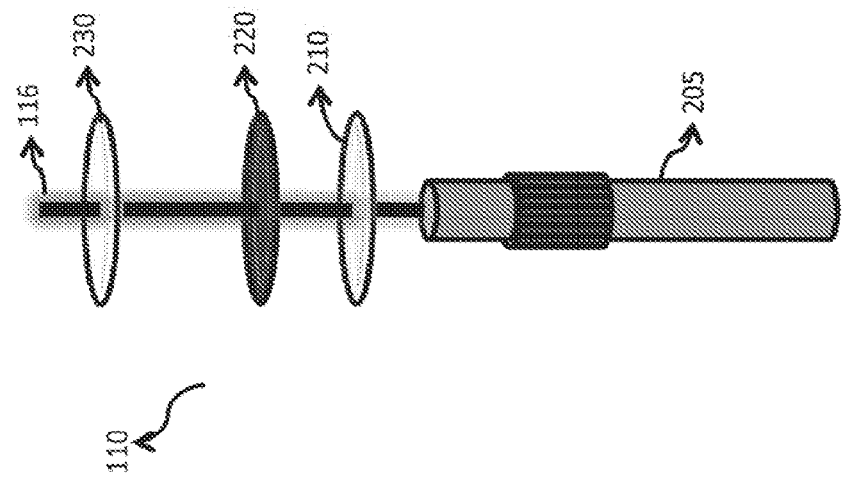

FIGS. 2A and 2B show exemplary embodiments of the illumination module 110. The illumination module 110 contains one or more illumination sources 205, along with optical elements for manipulating the beam (e.g., collimation or focusing) and appropriate filters. In one embodiment, one or more filters 210, 220, and 230 are used to select for band of wavelengths (i.e., spectral filters). In another embodiment, one or more filters 215 attenuates the intensity and power of illumination (i.e., neutral density filters) while one or more filters 225, 226, 227, 228, and 229 are used to select for a band of wavelengths. In one embodiment, selecting for a band of wavelengths is implemented to reject harmful wavelengths for a specific application (e.g., retinal imaging). For example, infrared wavelengths may be selectively blocked using a suitable filter. These filters may use any mechanism (e.g., absorption, reflection, etc.) to achieve the desired function. Filters can be mounted anywhere in the illumination path 116, though it is common to include them as close to the light source 205 as possible. In some embodiments, filters are mounted on one or more filter wheels 240 that rotate to invoke one or more of the filters or filter combinations. In some embodiments, filters are mounted on one or more filter slides that move linearly to invoke one or more of the filters or filter combinations. Movement of such filter wheels or slides may be manual, semi-automatic (i.e., motorized but user-triggered and/or controlled) or automatic (i.e., motorized and/or electronically controlled without user intervention).

The illumination sources 205 typically include the following types of illumination and wavelengths:
  (a) Red laser (approximate range: 625-655 nm)
  (b) Green laser (approximate range: 520-545 nm)
  (c) Blue laser (approximate range: 460-495 nm)
  (d) Near infrared (NIR) laser (approximate range: 700-900 nm)
  (e) White light illumination from LEDs, halogen lamps, etc.
  (f) Red, green, blue or NIR light from appropriate LEDs or achieved by spectrally filtering white light (wavelength ranges, as indicated for lasers, above).

In an embodiment designed for LSCI, the illumination source 205 in the OID 100 comprises one or more lasers or an equivalent coherent illumination source. In another embodiment designed for acquiring reflectance and/or fluorescence images or for viewing for interpretation or focusing (e.g., in preparation for image acquisition), the illumination source 205 is one or more incoherent illumination sources.

Not all applications will require the use of all illumination sources or illumination modalities. For example, green illumination mode can be achieved by switching on a white light source with a green filter in the optical path and an appropriate neutral density filter to attenuate the intensity to the desired value. Such a green illumination mode may be provided in the OID 100 to provide the user/operator/interpreter with more information about the FOV. The OID 100 may not necessarily use this mode during every use/operation. Likewise, elucidation of microvascular flow in the retina may require only a 635 nm (red) laser illumination to be invoked while segmentation of vessels into arteries and veins may require both the red laser as well as white illumination modes to be invoked sequentially.

The OID 100 may be used to perform fluorescence imaging, in which case the illumination source 205 and associated spectral filter will depend on the dye being used. For fluorescein angiography, the illumination will be in the blue region of the electromagnetic spectrum, that is, its wavelength will lie in the range between 460 nm and 495 nm. For indocyanine green (ICG) angiography, the illumination may lie between 700 nm and 820 nm. Specific illumination patterns can be created by switching "on" and "off" the appropriate light source, together with pre-assembled, manual, or motorized control of filter sets.

The illumination module 110 may also contain one or more apertures (e.g., pinhole aperture, slit aperture, or circular apertures) of various sizes for finer control of illumination. Such an aperture may be fixed or adjustable, much like the filters described above. For example, one embodiment can incorporate an aperture wheel, analogous to the filter wheel 240, which can be rotated to invoke the aperture appropriate for the desired illumination mode. Another embodiment can incorporate adjacent apertures which can be slid into and out of position for a similar purpose.

FIGS. 3A and 3B illustrate embodiments of the illumination module 110 comprising at least one coherent light source 306 (e.g., a laser) and one incoherent light source 306 (e.g., a halogen lamp). More sources may be added depending on the application. For example, instead of using a single white light LED in conjunction with a red filter and a green filter to obtain red and green light, two dedicated light sources (e.g., a green LED and a red LED) may be used. Alternatively, two white light LEDs with a dedicated red filter and a dedicated green filter, respectively, may be used.

FIG. 3A shows selective activation and deactivation of the light sources through mechanical indexing. A mechanical means may be included as part of the OID 100 that can orient each light source (along with associated filters) such that the emitted beam is along the illumination axis 115. The source may be moved with respect to the illumination axis 115, or the source may be kept fixed along the illumination axis 115 and filters and/or shutters moved with respect to the source to selectively appear in the illumination path 116. Indexing may be done manually or using linear/rotary motor(s) 320 with or without gear assemblies 325. In one embodiment, a stepper motor is used for tight and programmed control of the angle of rotation 335 or the distance of linear translation 330. Rotary motion can be used to engage the desired illumination source 305 or 306 using a stepper motor 320 located along 321 or orthogonal to 326 the indexing axis 310.

FIG. 3B shows selective activation and deactivation of the light sources through electronic switching. The illumination sources 305 and 306 may be immobilized in the illumination module 110 and their selective activation and deactivation may be performed by switching them "on" or "off" electronically through an illumination control module 340. Such a circuit may directly control the power fed to the illumination sources 305 and 306 and/or the timing of illumination (e.g., start time, duration, and duty cycle). A beam splitter 350 or equivalent arrangement allows the light from the illumination sources 305 and 306 to be oriented along the illumination axis 115.

The illumination module 110 can employ a combination of mechanical and electronic switching for enhanced control of the illumination sources 305 and 306. For example, the white light source may be switched "on" and "off" electronically, but red and green filters may be mechanically indexed in the path of the white light to achieve the red light illumination mode and the green light illumination mode respectively. The trigger for mechanical indexing or electronic switching or both may be manual, automatic, or semi-automatic. For example, in a manual embodiment, the user can rotate a spring loaded indexing mechanism to selectively engage the illumination source 305 and orient it along the illumination axis 115, while simultaneously disengaging the other illumination source 306. In an automatic embodiment, a pre-set timing sequence or other control mechanism may be used to selectively engage each source for a fixed amount of time. Such a timing sequence may be provided to the switch circuit through a processor or to a motorized indexing mechanism. In a semi-automatic embodiment, the user can move a desired filter into position, then press a push button that causes one illumination source 305 switch "off" after a period of time and another illumination source 306 to switch "on".

Figure 4:
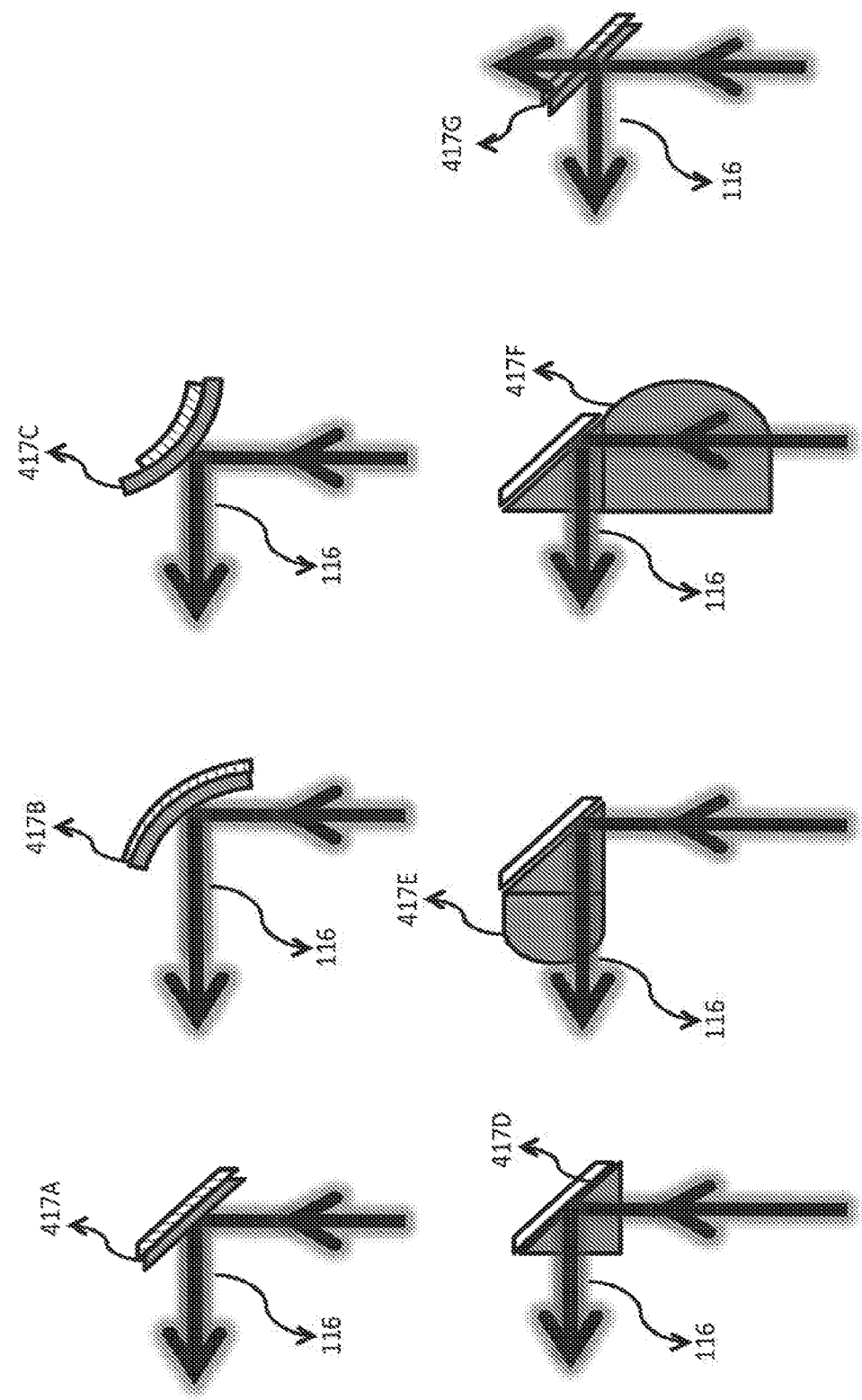
FIG. 4 illustrates various embodiments of the beam deflector.

FIG. 4 illustrates various embodiments of the beam deflector 117. The beam deflector 117 may be a plane mirror 417A, concave mirror 417B, or convex mirror 417C as long as the purpose served by the beam deflector 117 in conjunction with the illumination module 110 and Optical Assembly A 120 is to produce a beam of light convergent at or just in front of the target tissue (for imaging of the front of the eye) or the pupil (for imaging the back of the eye). In one embodiment for imaging of the retina, the beam deflector 117, illumination module 110, and Optical Assembly A 120 are configured to produce a beam of light convergent at or just in front of the pupil of the subjects eye 170. The beam deflector 117 function could also be achieved using a prism 417D or combination of prisms 417E and 417F made of an optically transparent element, such as a glass or plastic that uses total internal reflection to deflect the beam of light in the desired direction. Likewise, it is also possible to combine or fuse the beam deflector 117 with elements of Optical Assembly A 120 and/or Optical Assembly B 130. The beam deflector 117 may also be a beam splitter 417G that reflects a portion of the light incident on it, while transmits the remainder.

Figure 5A:
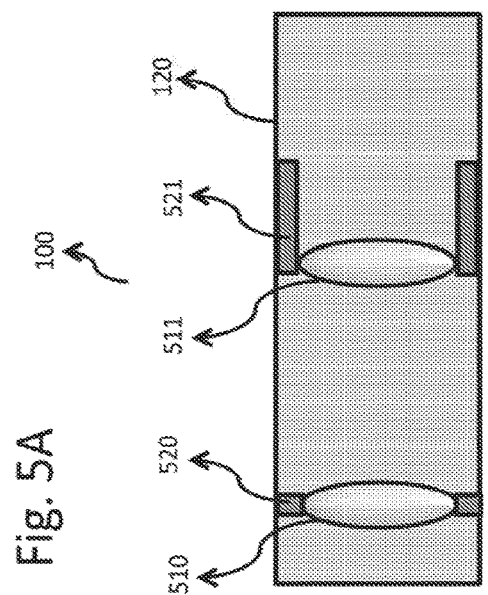
FIGS. 5A, 5B, and 5C illustrate various embodiments of the Optical Assembly A and its relation to the field of view of the target tissue illuminated by the OID.
Figure 5B:
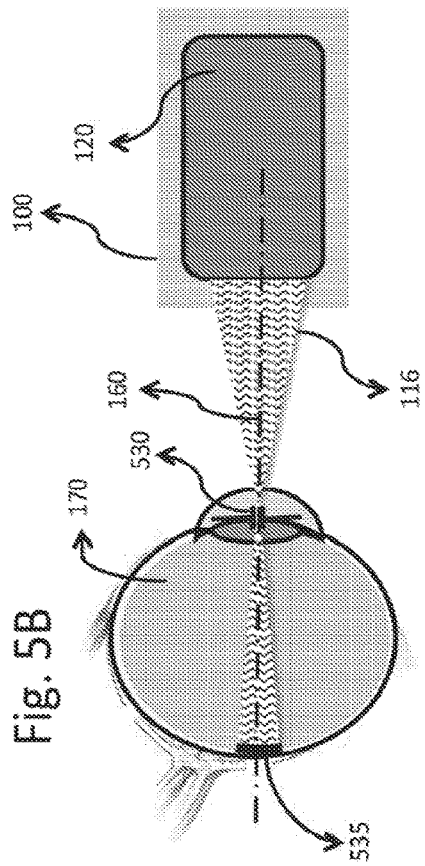
Figure 5C:
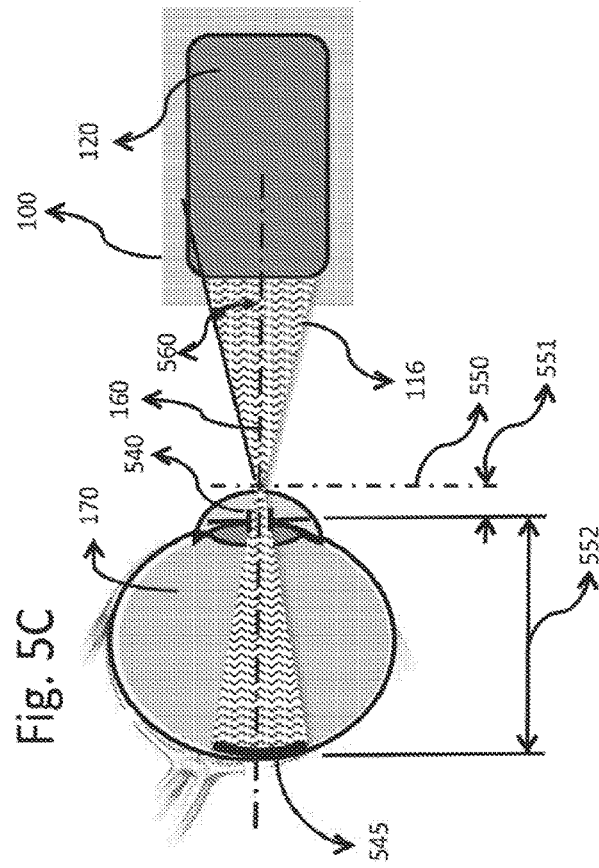

FIGS. 5A, 5B, and 5C illustrate various embodiments of the Optical Assembly A 120 and its relation to the FOV of the target tissue 175 illuminated by the OID 100. In some embodiments, the Optical Assembly A 120 influences both the illumination path 116 as well as the imaging path 135 and may contain one or more optical elements (e.g., lenses, filters, mirrors, collimators, beam splitters, fiber optics, and light sensors) to direct light along the illumination path 116 to the target tissue 175 and light along the imaging path 135 to the image acquisition module 140.

FIG. 5A shows an exemplary Optical Assembly A 120 of an OID 100 that contains two lenses 510 and 511. In some embodiments, the Optical Assembly A 120 contains one lens, while in other embodiments the Optical Assembly A 120 contains more than one lens. All or some of the lenses can be fixed or adjustable. In this embodiment, the location of one lens 510 is fixed by a mechanical mount 520 while the second lens 511 is attached to an adjustable mount 521, which can be controlled manually, semi-automatically, or automatically. This exemplary embodiment can also describe the embodiment of Optical Assembly B 130.

FIGS. 5B and 5C show the influence of pupil dilation on the FOV (i.e., the area of the target tissue 175 that is imaged). Illuminating the back of the subject's eye 170 through an undilated or narrow pupil 530 results in a small FOV 535. Conversely, illuminating the back of the subject's eye 170 through a dilated or wide pupil 540 results in a large FOV 545.

In an embodiment that uses LSCI to image the retina, the Optical Assembly A 120 can be designed such that: (a) the FOV is as large as possible, (b) the light intensity at the retina never exceeds a safety threshold, (c) the desired imaging technique can be achieved through the subject's dilated or undilated pupil, and (d) the subject's pupil does not become critical in determining the speckle size. To meet the objectives (a), (b) and (c), the effective focal length of Optical Assembly A 120 should be less than 25 mm. In this embodiment, the illumination beam will converge at the pupil or just in front of the pupil, so that light entering the eye is a divergent beam and illuminates a large FOV 525. The distance 552 between the retina and the pupil is approximately 20 mm in human adults, and a beam diverging over this distance will decrease the risk of over exposure at the retina (than a beam that is convergent or parallel over the same distance). The undilated (and also unconstricted) pupil 530 is approximately 3-4 mm in diameter in human subjects. Thus, a circular region with diameter of ~1 cm on the retina can be illuminated if Optical Assembly A 120 converges the illumination path 116 such that the half-angle ψ 560 that the beam envelope makes with the imaging axis 180 is greater than 11 degrees. Much of the illuminating light will enter the pupil if the point where the beam diameter is the smallest lies on the focal plane 551 5-7 mm from the pupil.

In another embodiment, illumination of the entire FOV 525 may be achieved through illumination of multiple smaller overlapping areas on the target tissue 175. The advantage of such an arrangement is to prevent the illumination beam from being centered at the imaging axis 180 (called off-center illumination) so that back reflection from elements of Optical Assembly A 120 or non-relevant portions of the target tissue 175 (e.g., reflection from the cornea when the target tissue is the retina) is reduced, increasing contrast at the imaging sensor 145. In one embodiment, annular illumination at the pupil 530 is employed to achieve off-center illumination. In another embodiment, the illumination beam is split into multiple illumination beams, each of which is not coaxial with the imaging axis, and Optical Assembly A 120 is utilized to focus each of these multiple illumination beams to converge at or in front of the pupil 530 (e.g., on the focal plane 551) but not on the imaging axis 180 as described above. In this embodiment, the resulting illumination of the entire FOV 525 will be produced by the superposition of the individual and overlapping FOVs of each of these multiple illumination beams.

The above calculations for increasing the FOV without pupil dilation are explained on the basis of the geometry of an average healthy human adult, but the same can be achieved for varying eye sizes and eye conditions and for each type of illumination used in the embodiment. Such an optimization may produce various embodiments each suited for specific cases. For example, an OID 100 for imaging the eyes of cats and dogs (i.e., veterinary use) may employ a different embodiment than the embodiment used for imaging human adults. Similarly, an OID 100 may employ a different embodiment for imaging infant (premature or otherwise), toddler, pre-pubescent, or adolescent eyes. The OID 100 may employ an Optical Assembly A 120 with adjustable elements that can be tuned for the subject and application prior to imaging. In one embodiment, an opaque eye covering unit can be used to prevent ambient light from reaching the subject's eye 170 so as to cause natural pupil dilation, improving the FOV illuminated and imaged.

Figure 6:
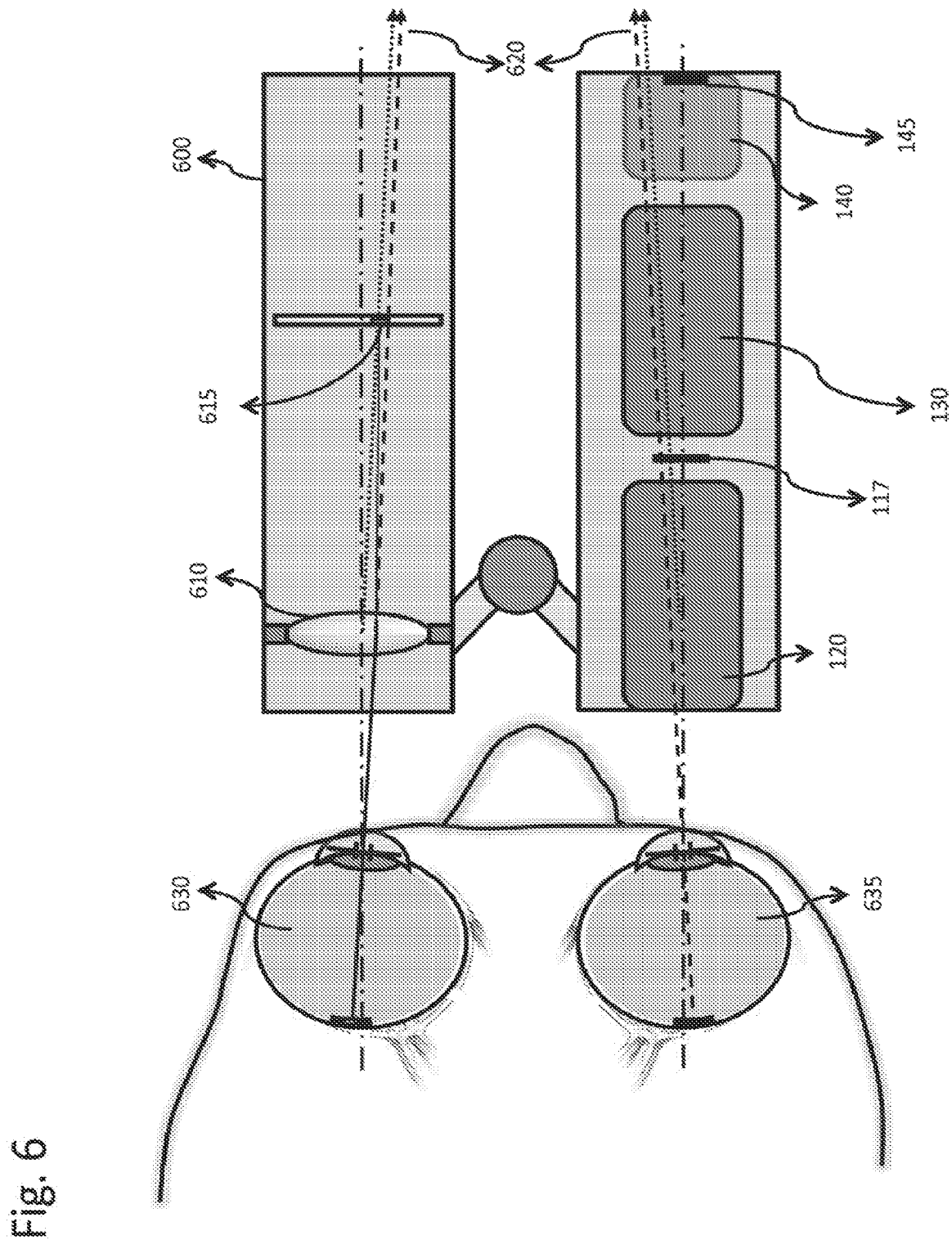
FIG. 6 is a schematic of the OID and an embodiment of a mechanism used to induce a subject to fixate the gaze to facilitate image acquisition.

FIG. 6 shows a schematic of the OID 100 and an embodiment of a mechanism used to induce a subject to fixate the gaze to facilitate image acquisition of the appropriate region of the target tissue 175. To reduce the variability in the focal length of the subject's eyes, the subject can be instructed to fixate his/her gaze using the non-imaged eye 630, on an object that is far (for example, greater than 5 meters, an approximation for infinity) or at a virtual image of a dummy object that achieves the same effect. Such a virtual image 615 can be produced using appropriate optics by a module in the OID 100. In this embodiment, an optical system 600 is positioned in front of the non-imaged eye 630 for gaze fixation. The optical system 600 includes an optical assembly that comprises one or more lenses and an object 615 localized at a depth close to the focal plane of the optical assembly. In the focal plane, the object's coordinates may be predetermined or determined by the user at the time of imaging. Placing the object in the focal plane will cause the subject's eye to visualize the virtual image (O') 615 of the object formed far away (greater than 5 meters). If the object is placed precisely in the focal plane, the image will be theoretically formed at 'infinity'. Due to natural tendency, the imaged eye 635 will also focus at the same depth, thus setting the focal length of the imaged eye 635 within an expected range. Such a focal length of a set of eyes fixated on an image that is far away would be approximately equal to the diameter of the eye, that is, approximately 20 mm for an average human adult (smaller for younger humans and smaller animals). The in-plane positioning ($x_0$, $y_0$) of the object will determine the angle of the optical axis of the eye with respect to the optical axis of the OID. Thus, by choosing ($x_0$, $y_0$), it becomes possible to image different regions of the retina—that is, the imaged FOV may now include some peripheral regions that would not lie within the FOV otherwise. The object may thus be replaced by a screen or a two-dimensional photograph and the subject be instructed to fixate on some predetermined features prior to each imaging event.

FIG. 7 illustrates an exemplary embodiment for immobilizing the OID 100 with respect to the subject's eye 170. In some embodiments, the OID 100 attaches temporarily or permanently to a rigid component (e.g., a nose-bridge, rubber cup, sunglasses, or goggles) that immobilizes the OID 100 with respect to the imaging target. In some embodiments, the rigid component is designed to block ambient light from reaching the eye, creating an artificial dark environment to cause natural pupil dilation. A gaze fixation device 600 can be incorporated into the embodiment as a temporary or permanent attachment to the rigid component. In this embodiment, the rigid component is a pair of eyeglasses 700 used to minimize motion artifact by resting stably on the nose-bridge and the ears while imaging is performed. In another embodiment, optical fibers can guide light from the illumination module 110 bidirectionally to and from the eyeglasses 700 and the OID 100. In another embodiment, waveguides etched into the plastic or glass of the eyeglasses can guide light from the illumination module 110 bidirectionally to and from the subject's eye.

Figure 8B:
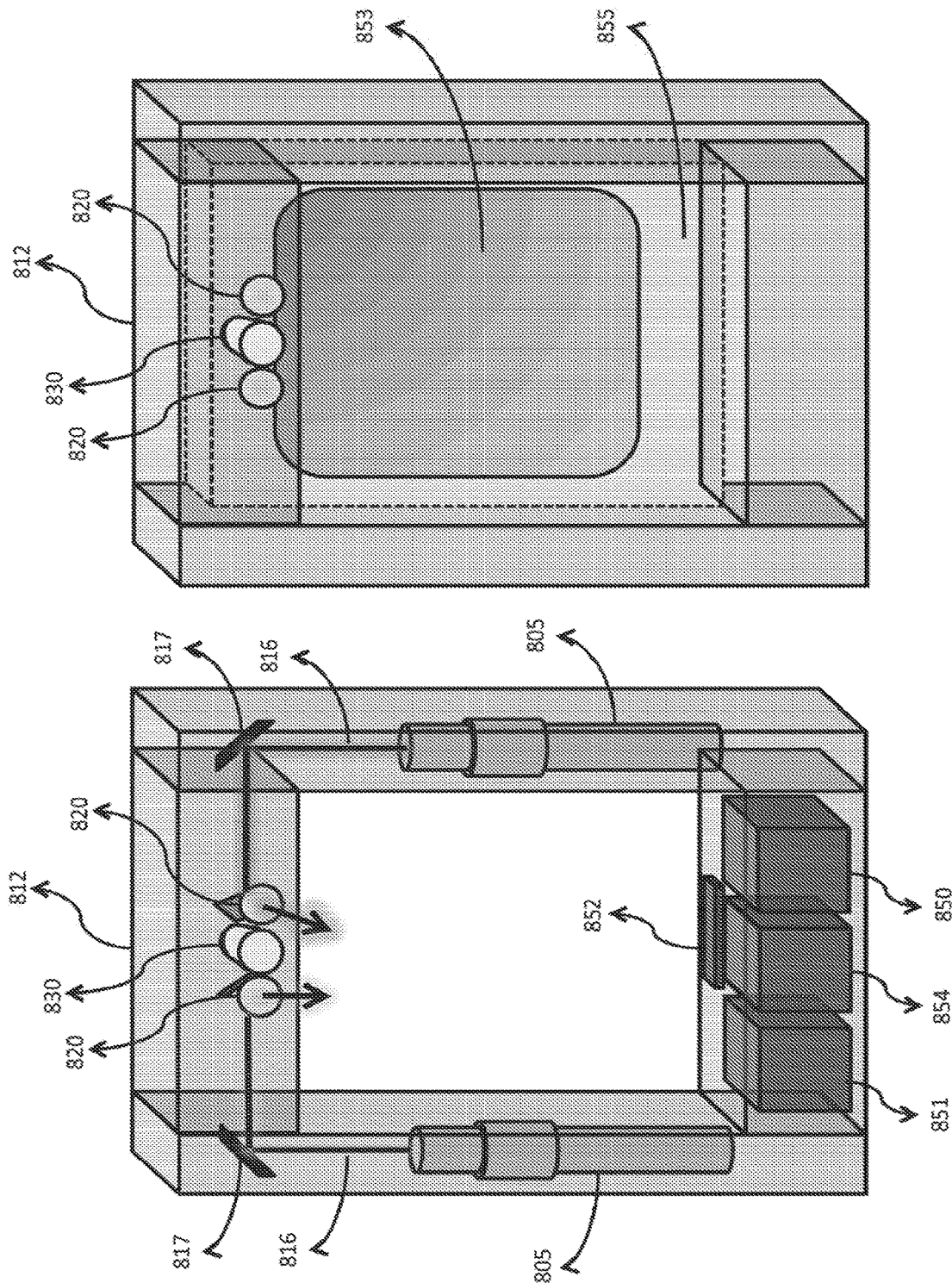

FIGS. 8A and 8B illustrate various embodiments for the incorporation of an OID 810 into a standalone system 800 that can be operated by non-experts using a simple user interface 820. FIG. 8A illustrates one embodiment in which the user interface 820 is a touch screen that automates the image acquisition, storage, and transmission processes. Such a user interface 820 may also include a method for accepting payment (e.g., a credit card reader) to bill the customer for the imaging services. In this embodiment, the OID 810 is stationary, thus permitting the subject to position his/her eye(s) in alignment with the imaging axis and rest the head/face against a rigid support to mitigate motion artifact. In another embodiment, the OID 811 is connected through electrical cables and/or optical fibers to a rigid object that rests on the subjects' head (e.g., a helmet, goggles, glasses). In this embodiment, some elements of the OID 811 can be contained in the housing of the interface 820.

FIG. 8B illustrates an embodiment in which an OID 812 is used in conjunction with a mobile computing platform 855 (e.g., a smartphone or tablet computer). In this embodiment, the mobile computing platform 855 contains one or more power modules, processor modules, image acquisition modules, communications modules, storage modules, and user interface modules 853. The communications module of the mobile computing platform 855 can include either wireless or wired mechanisms or both. In this embodiment, the OID 812 contains one or more illumination modules 805, one or more beam deflectors 817 to direct the one or more illumination paths 816 toward the one or more Optical Assembly A 820, one or more Optical Assembly B 830, and one or more processor modules 850. The OID 812 can contain a telemetry module 851 to communicate with the mobile computing platform 855 or to an external device. The OID 812 can contain a power module 854 to power some or all of the electronic elements of the OID 812 or the mobile computing platform 855. The OID 812 can connect to and communicate with the mobile computing platform 855 through a wired mechanism 852. In another embodiment, some or all of the processing capabilities can be performed using the mobile computing platform 855. In another embodiment, the mobile computing platform 855 can be used to replace or provide alternate capabilities of some or all of the power modules, processor modules, image acquisition modules, communication modules, storage modules, and illumination modules.

Figure 9:
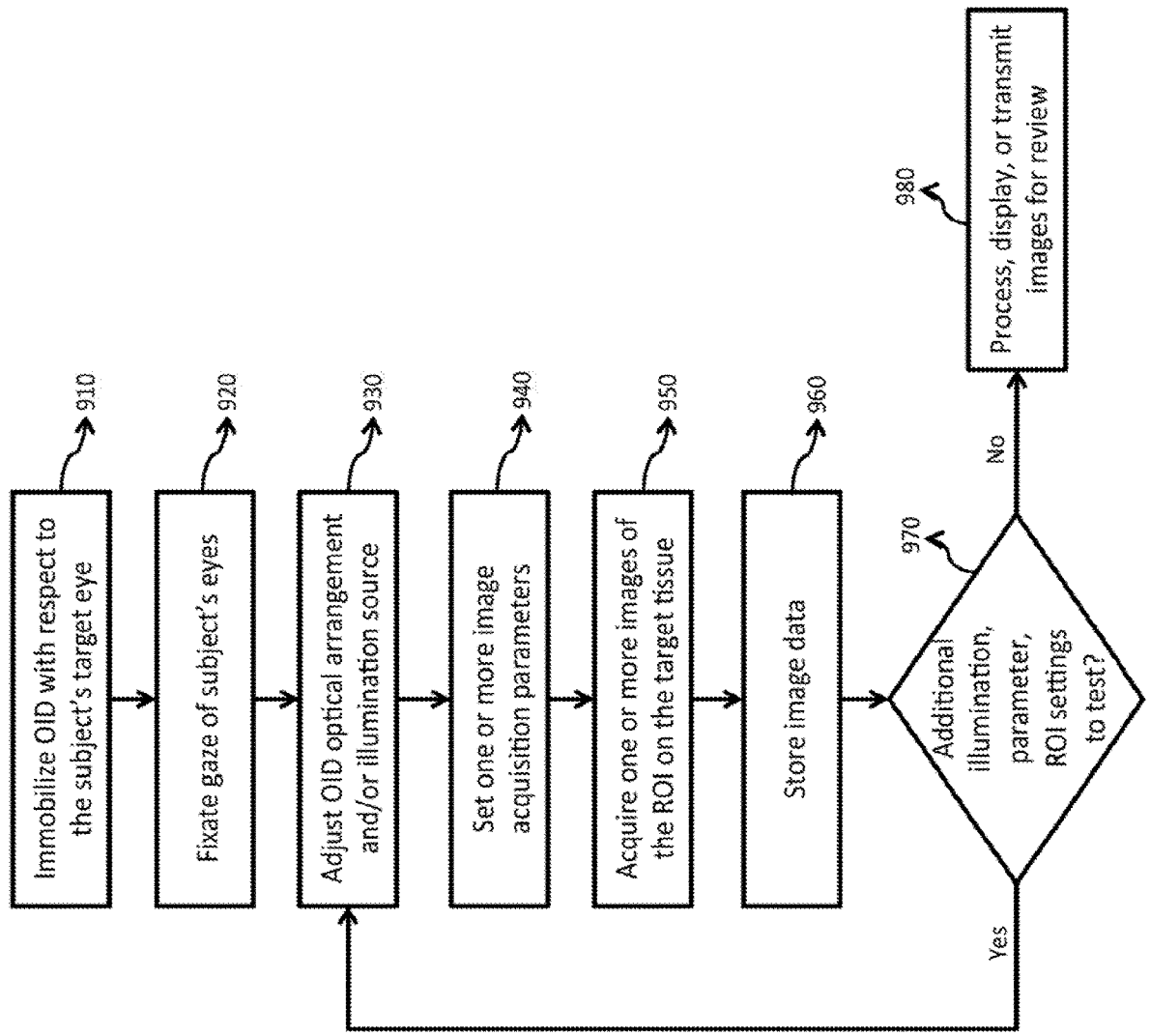
FIG. 9 is a flowchart illustrating a method for using the OID to acquire images of the target tissue in accordance with the embodiments of the subject technology.

FIG. 9 is a flowchart illustrating a method for using the OID 100 to acquire images of the target tissue 175 in accordance with the embodiments of the subject technology. The first step 910 is to immobilize the OID 100 with respect to the subject's eye 170. This immobilization step 910 can be achieved manually with either the operator holding the OID 100 as steady as possible, positioning the face against the OID 100 as steady as possible, or using one of various embodiments (e.g., chin rest, eyeglasses, goggles, or a helmet) that achieve a similar function. In one embodiment, this immobilization step 910 is achieved through the use of a covering that rests gently on the face around the eye.

The second step 920 involves fixating the subject's gaze on a target that is either predetermined or determined dynamically by the operator. In both cases, fixation can be achieved through control of the gaze fixation mechanism 600. In some cases, the subject may also be the operator (e.g., in the case of a standalone system).

The third step 930 is to adjust one or more of Optical Assembly A 120 and Optical Assembly B 130 such that an image is formed on the imaging sensor 145 with acceptable focus and clarity. In this third step 930, the illumination module 110 may also be adjusted (e.g., to achieve the appropriate type of illumination and the appropriate intensity of illumination). In one embodiment, the illumination module 110 is adjusted to invoke white or green light illumination. The adjustment of one or more of Optical Assembly A 120, Optical Assembly B 130, and the illumination module 110 may be done manually by the operator, semi-automatically, or automatically by the processor unit 150.

The fourth step 940 includes setting of one or more of the following image acquisition parameters: exposure time, gain (or pixel sensitivity), number of images, frequency of image frame acquisition (or frame rate), timing sequence, and pixel resolution and/or pixel area. Exposure time over which the imaging sensor 145 integrates light has a direct bearing on sensitivity and saturation of images during an imaging session. Exposure time also determines the level of proportionality between laser speckle contrast and velocity of light scatterers (e.g., red blood cells) in the imaged specimen. Exposure times that are smaller than 100 milliseconds are typical for LSCI. Exposure times for fluorescence imaging may be longer (up to 2 seconds). Gain (or sensitivity of pixel output to light intensity) of the imaging sensor 145, in some embodiments, may be adjustable. In such embodiments, the adjustable gain mechanism allows, for the same number of photons reaching the imaging sensor 145, the output of the imaging sensor 145 to be higher or lower depending on the gain value. The number of images refers to the total images acquired in an image stack for a given image acquisition. The number of images can be one or more for a given ROI. Frequency of image frame acquisition (frame rate) is the number of image frames to be acquired in 1 second and often depends on the image acquisition device and its ability to communicate with a temporary or permanent storage device. In some CMOS cameras, for example, it is possible to achieve a frame rate that is the inverse of the camera exposure time. Timing sequence refers to specific times or time intervals for which the imaging sensor 145 acquires images and may incorporate appropriate time delays between subsequent image acquisitions. Pixel resolution and/or pixel area refers to the number of pixels that are used to capture an image of the ROI. For example, the entire extent of a certain ROI 6.4 mm×5.12 mm in size may be acquired at a reduced 640 pixel×512 pixel resolution as opposed to a high 1280 pixel×1024 pixel resolution by setting 2×2 high-resolution pixels as one modified low-resolution pixel. In this case, the imaged area remains the same. Also, only 640×512 contiguous high-resolution pixels may be used to obtain one-fourth the extent of the ROI. In this case, the pixel resolution is still high but the imaged area (or pixel area) decreases.

The fifth step 950 is to acquire one or more images of the ROI under the illumination parameters established in the fourth step 940.

The sixth step 960 is to store the images acquired in the fifth step 950 for subsequent processing. In some embodiments, these acquired images can be stored locally on the OID 100 (e.g., RAM, magnetic or solid state hard disk technology, flash disk technology, or optical disk technology). In some embodiments, these acquired images can be stored remotely on an external storage device. In some embodiments, these acquired images can be stored temporarily on the OID 100. Local storage can be achieved using a memory element permanently or temporarily embedded in the OID 100. Remote storage involves the use of a data transmission channel.

The seventh step 970 is to determine whether additional images must be obtained under different settings (e.g., under a different illumination modality, adjustment parameter, or ROI). In one embodiment, after acquiring a reflectance image of the retina, the illumination module 110 is adjusted to green or red laser illumination for the OID to be able to perform LSCI. The third step 930 through the sixth step 960 are repeated as necessary for the desired application.

The last step 980 is to process the images acquired in the fifth step 950. In some embodiments, this last step 980 consists of one or more of the following:

Processing for LSCI. Speckle contrast may be calculated as the ratio of standard deviation and mean of pixel intensities in a neighborhood of pixels. The neighborhood of pixels around a pixel P may be derived from either or both of spatial and temporal domains, that is the pixels comprising the neighborhood may be spatially adjacent to the pixel P, or the pixels comprising the neighborhood may lie at the same location as P but in adjacent (in time) image frames, or the pixels comprising the neighborhood may lie both spatially adjacent to pixel P in the same frame and also in adjacent frames. The speckle contrast values may also be averaged either spatially or temporally. The neighborhood may be spatially isotropic, where the neighborhood may comprise the same number of pixel in every direction about the pixel P, or anisotropic, where the neighborhood be preferentially oriented in one or more directions (e.g., along the direction of blood flow in vessels, or along the axial direction of blood vessels). Various ways of choosing neighborhoods and calculating laser speckle contrast is described in (1). The speckle contrast may be used, for example, to:

Obtain high-resolution images of blood vessels in the eye with high distinguishability from the background tissue, in healthy situations as described for brain vasculature in (2), as well as in abnormal situations as described for skin vasculature in (3);

Obtain images of blood flow in the eye, as described for brain vasculature in (4); and Obtain images of microvessel density in one or more regions of the eye, as described for brain tumor vasculature in (5).

Feature extraction using a combination of one or more of LSCI, spectroscopic, and fluorescence images. This processing method may include:

vessel segmentation using intensity-based thresholds, ridge detection, or ridge tracking algorithms;

extracting vessel centerlines using morphological operations on the segmented vessels;

diameter estimation using edge detection techniques, or ridge detection techniques, as described for brain/meningeal vasculature in (6);

distinguishing between arteries and veins using a combination of spectroscopic images (in which arteries and veins have different light absorption properties) and LSCI images (in which arteries and veins have different blood velocities).

Any of the processing methodologies disclosed in prior art (7) and (8).

Registration of the acquired images to one another. The said registration may be done for multiple images of the same ROI, as is implemented in (9) for mitigating the effect of motion artifact on LSCI; or for images of adjacent ROIs to build a mosaic or panoramic view of a larger ROI. Registration of acquired images to one another may be achieved prior to laser speckle contrast calculation, though an intermittent calculation of speckle contrast may facilitate the identification of features useful for registration, as described in (9).

Spectroscopic imaging. This processing method includes combining images obtained under different illumination either pixel-wise or feature-wise using a combination of mathematical functions (e.g., addition, subtraction, scalar multiplication, and power functions). Images may be normalized based on mean or a certain percentile of intensity values within the image or image stack, before the processing is done.

In some embodiments, this last step 980 consists of preparing the images acquired in the fifth step 950 for display on the OID 100 or an external display device (e.g., a smartphone, tablet, laptop, or other computing platform). In some embodiments, this last step 980 consists of transmitting the images acquired in the fifth step 950 for further processing on an external computing platform. In some embodiments, this last step 980 consists of a combination of the processing methods described above. In some embodiments, the processed images are stored locally on the OID 100 or on an external computing platform, or a combination thereof.

Figure 10:
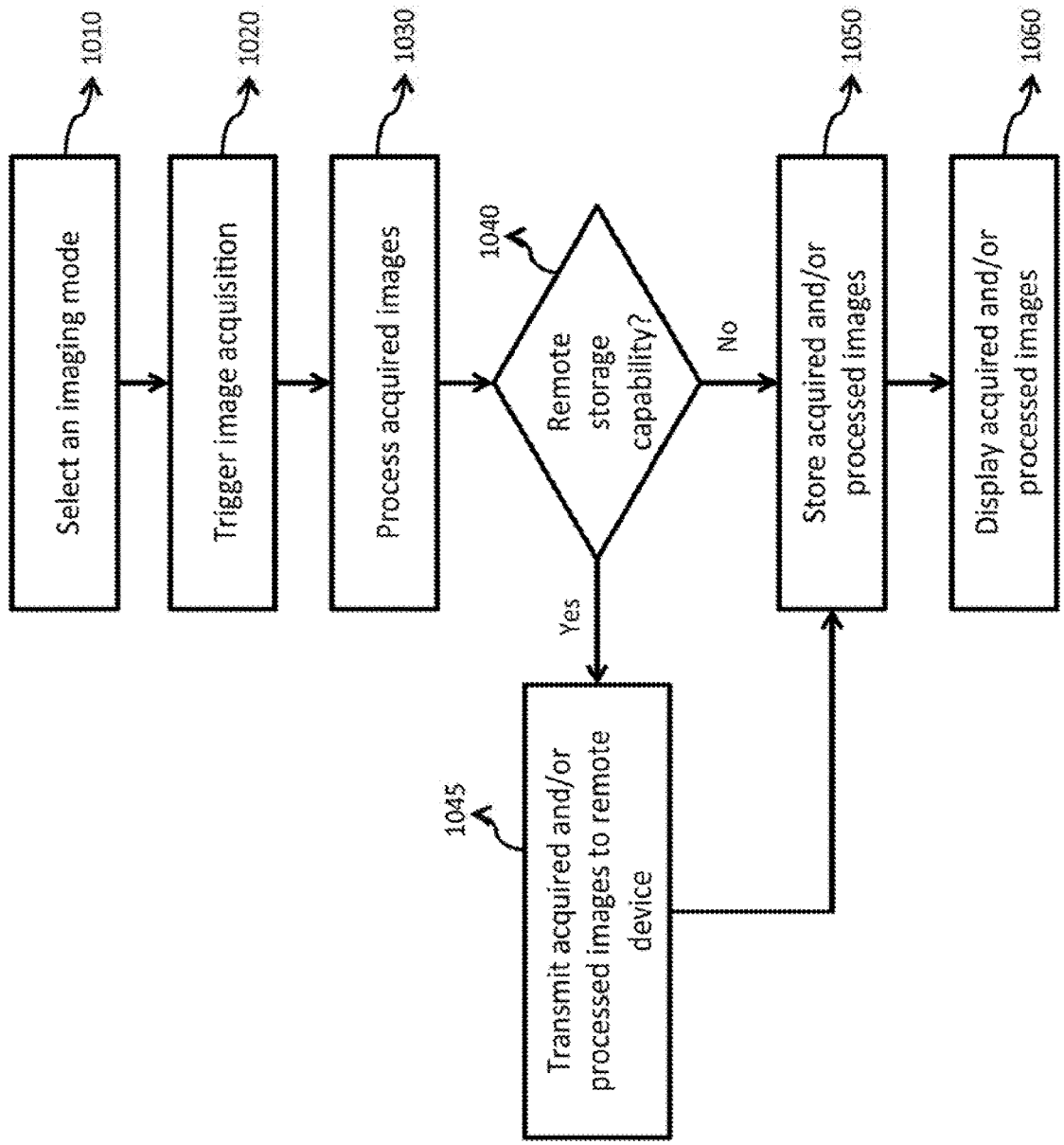
FIG. 10 is a flowchart illustrating a method for acquiring, processing, storing, and displaying the images obtained using the OID.

FIG. 10 is a flowchart illustrating the method for acquiring, processing, storing, and displaying the images obtained using the OID 100. In this embodiment, the first step 1010 is to select an imaging mode, which includes one or more of the following:

Laser speckle contrast imaging.
Spectroscopic imaging.
Reflectance imaging.
Fluorescence imaging.

The second step 1020 is to trigger the acquisition of one or more images using the one or more imaging modes selected in the first step 1010. The acquisition of one or more images in the second step 1020 can be triggered manually, semi-automatically, or automatically.

The third step 1030 is to process the acquired images. In some embodiments, this third step 1030 consists of one or more of the following:

Processing for LSCI. Speckle contrast may be calculated as the ratio of standard deviation and mean of pixel intensities in a neighborhood of pixels. The neighborhood of pixels around a pixel P may be derived from either or both of spatial and temporal domains, that is the pixels comprising the neighborhood may be spatially adjacent to the pixel P, or the pixels comprising the neighborhood may lie at the same location as P but in adjacent (in time) image frames, or the pixels comprising the neighborhood may lie both spatially adjacent to pixel P in the same frame and also in adjacent frames. The speckle contrast values may also be averaged either spatially or temporally. The neighborhood may be spatially isotropic, where the neighborhood may comprise the same number of pixel in every direction about the pixel P, or anisotropic, where the neighborhood be preferentially oriented in one or more directions (e.g., along the direction of blood flow in vessels, or along the axial direction of blood vessels). Various ways of choosing neighborhoods and calculating laser speckle contrast is described in (1). The speckle contrast may be used, for example, to:

Obtain high-resolution images of blood vessels in the eye with high distinguishability from the background tissue, in healthy situations as described for brain vasculature in (2), as well as in abnormal situations as described for skin vasculature in (3);

Obtain images of blood flow in the eye, as described for brain vasculature in (4); and Obtain images of microvessel density in one or more regions of the eye, as described for brain tumor vasculature in (5).

Feature extraction using a combination of one or more of LSCI, spectroscopic, and fluorescence images. This processing method may include:

vessel segmentation using intensity-based thresholds, ridge detection, or ridge tracking algorithms;

extracting vessel centerlines using morphological operations on the segmented vessels;

diameter estimation using edge detection techniques, or ridge detection techniques, as described for brain/meningeal vasculature in (6);

distinguishing between arteries and veins using a combination of spectroscopic images (in which arteries and veins have different light absorption properties) and LSCI images (in which arteries and veins have different blood velocities).

Any of the processing methodologies disclosed in prior are (7) and (8).

Registration of the acquired images to one another. The said registration may be done for multiple images of the same ROI, as is implemented in (9) for mitigating the effect of motion artifact on LSCI; or for images of adjacent ROIs to build a mosaic or panoramic view of a larger ROI. Registration of acquired images to one another may be achieved prior to laser speckle contrast calculation, though an intermittent calculation of speckle contrast may facilitate the identification of features useful for registration, as described in (9).

Spectroscopic imaging. This processing method includes combining images obtained under different illumination either pixel-wise or feature-wise using a combination of mathematical functions (e.g., addition, subtraction, scalar multiplication, and power functions). Images may be normalized based on mean or a certain percentile of intensity values within the image or image stack, before the processing is done.

The fourth step 1040 is to determine whether storage of the acquired images is external from the OID 100. If remote storage of the acquired images is selected in the fourth step 1040, then the next step 1045 is to transmit one or more of the acquired and/or processed images to the remote storage device.

The fifth step 1050 is to store one or more of the acquired and/or processed images in the selected storage location. In some embodiments, the selected storage location is embedded permanently or temporarily in the OID 100. In some embodiments, the selected storage location is one or more external storage systems, including, for example, a smartphone, tablet, laptop, cloud computing system (e.g., a remote patient monitoring system or a mobile disease management system), or other computing platform (e.g., desktop computer or web server). The OID 100 can connect to the one or more selected storage locations via a combination of wired or wireless means.

The sixth step 1060 is to display the acquired and/or processed images for review by the user. The display can consist of one or more of a liquid crystal display (LCD) screen or its equivalent embedded in the OID 100 or a similar screen embedded in an external system (e.g., a smartphone, tablet, laptop, or other computing platform). The sixth step 1060 can include the use of display software to facilitate visualization of the acquired and/or processed images or to allow the user to manipulate the acquired and/or processed images.

The second step 1020 through the sixth step 1060 can be repeated sequentially or simultaneously for each imaging mode selected in the first step 1010.

Figure 11:
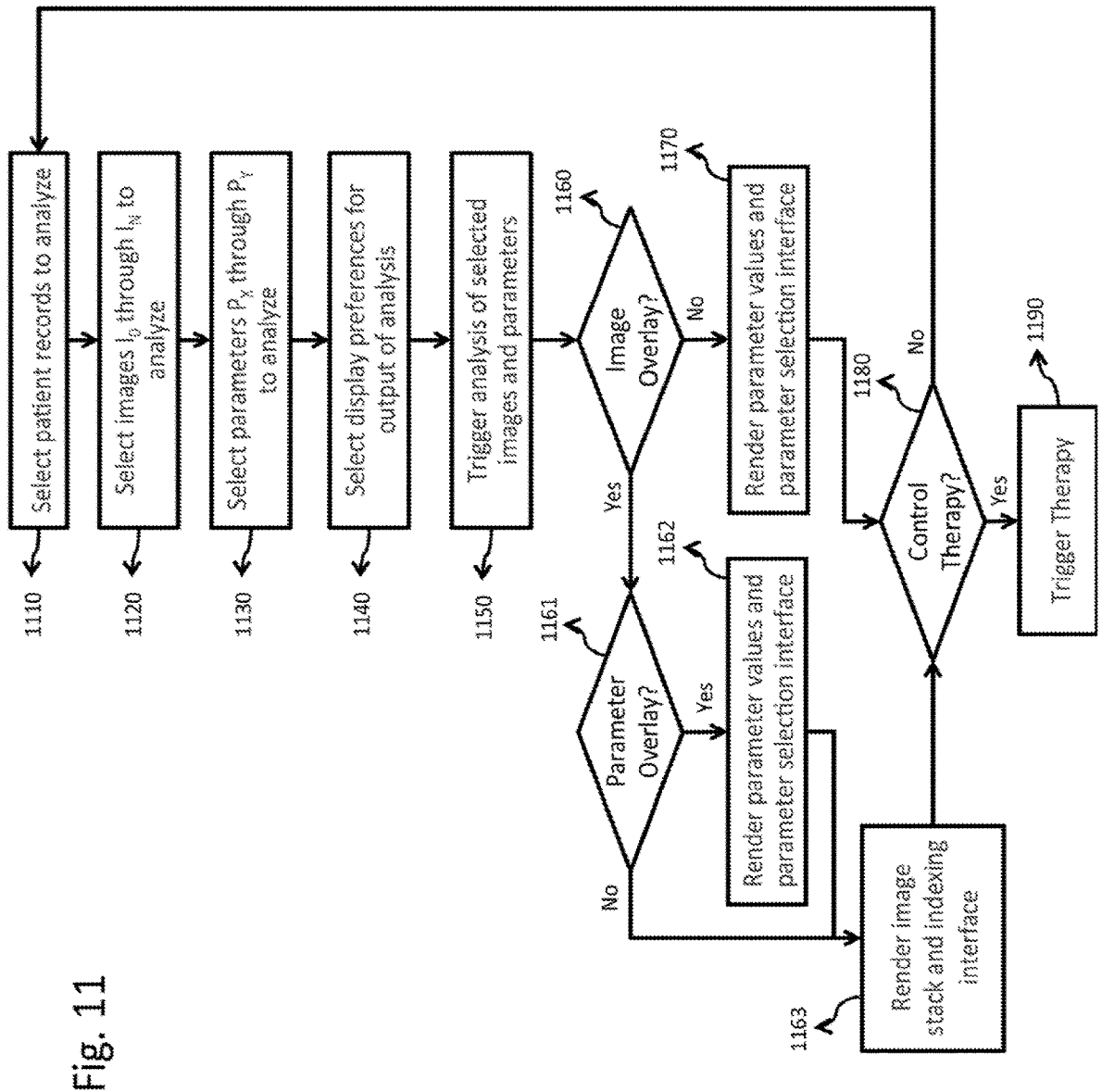
FIG. 11 is a flowchart illustrating a method for analyzing images obtained using the OID for disease progression assessment and management.

FIG. 11 is a flowchart illustrating a method for analyzing images obtained using the OID 100 and stored in an electronic patient record system for disease progression assessment and management. In this embodiment, the first step 1110 is to select a patient record to analyze. The second step 1120 is to select one or more of images ($I_O$ through $I_N$) stored in the patient's record for further analysis. In one embodiment, the images selected for analysis were obtained using an OID in the LSCI mode. The third step 1130 is to select one or more parameters ($P_X$ through $P_Y$) extracted from, for example, a combination of one or more of LSCI, spectroscopic, reflectance, and fluorescence images. Examples of parameters $P_X$ through $P_Y$ are blood flow, blood vessel diameters, microvessel density, and blood oxygenation. The fourth step 1140 is to select display preferences for presentation of the output of the analysis. The fifth step 1150 is to trigger analysis of the one or more of the images and/or parameters selected in the second step 1120 and the third step 1130. The next step 1160 uses information from the display preferences from the fourth step 1140 to determine whether to display the images in an overlay format. The next step 1161 uses information from the display preferences from the fourth step 1140 to determine whether to display parameters in an overlay format. If the display preferences selected in the fourth step 1140, the next steps 1162 and 1163 are to render the parameter values and image stack along with an interface for navigating through the images and an interface for selecting/de-selecting parameters to be rendered. If the display preferences from the fourth step 1140 do not include the image overlay option, the next step 1170 is to render the parameter values along with an interface for selecting/de-selecting parameters to be rendered. If the display preferences from the fourth step 1140 include the image overlay option but not the parameter display option, the next step 1163 is to render the images without rendering parameter values. The last step 1190 is to trigger therapy manually, semi-automatically, or automatically based on the one or more analyzed images and/or parameters. In one embodiment, the last step 1190 consists of a recommendation to the user to change a specific drug medication or to perform some other treatment procedure. In another embodiment, the last step 1190 consists of a recommendation that allows the user to trigger an automatic treatment or procedure (e.g., an electronic prescription). In another embodiment, the last step 1190 consists of an automated signal that controls a treatment mechanism (e.g., laser photocoagulation).

Figure 12A:
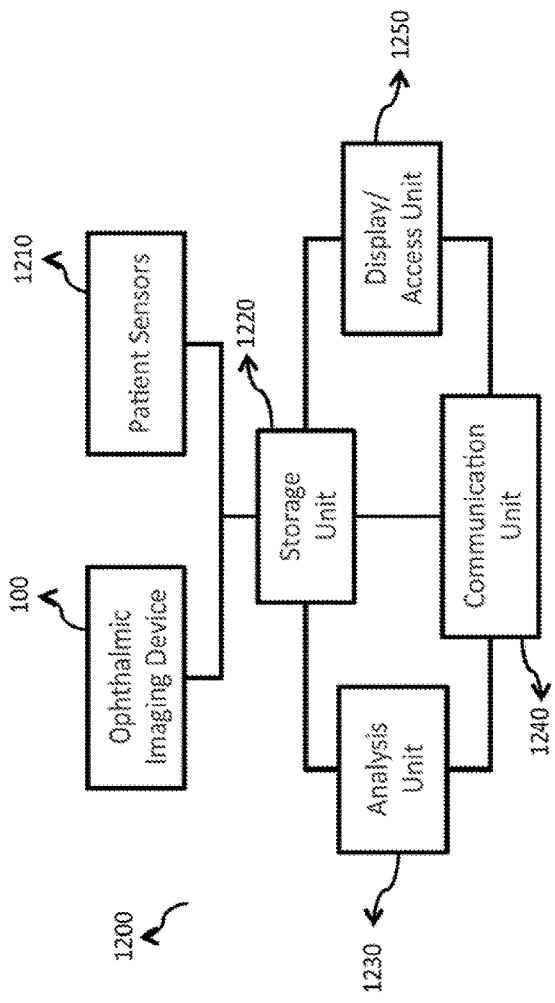
FIGS. 12A and 12B are schematics for various embodiments of a disease monitoring and management system incorporating the OID.
Figure 12B:
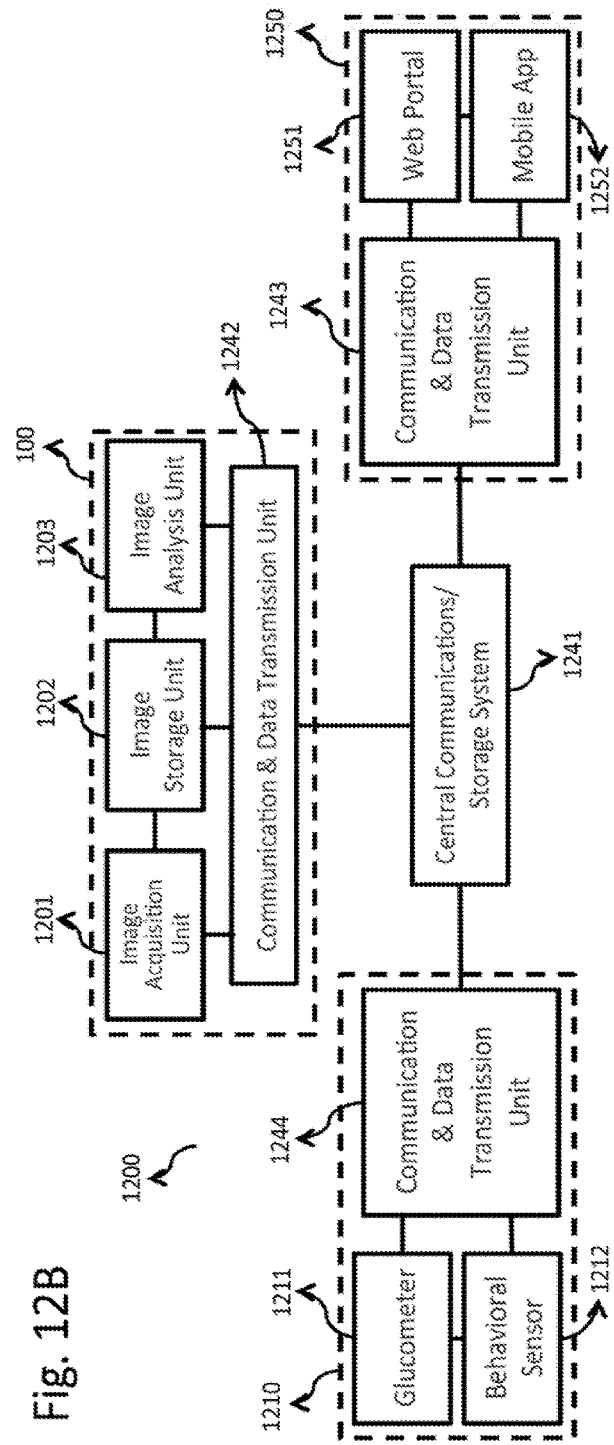

FIGS. 12A and 12B are schematics for various embodiments of a disease monitoring/management system 1200 incorporating the OID 100. As shown in FIG. 12A, a disease monitoring/management system 1200 can incorporate one or more sensors, processors, storage units, interfaces, and data communication mechanisms and be used for the purpose of facilitating the monitoring of a patient by a remote caregiver or managing diagnosis or treatment of one or more diseases (e.g., diabetes, hypertension, DR, HR, ROP, AMD, retinal detachment, glaucoma, cataract, choroidal neovascularization). In one embodiment, the disease monitoring/management system 1200 is designed for management of diabetes and includes an OID 100 and other diabetes sensors 1210 (e.g., blood glucose meters, continuous glucose monitors, infusion pumps, weight scales, exercise sensors, food consumption sensors, electronic journals, EHRs, and laboratory information systems (LIS)). Data from these sensors 100 and 1210 (e.g., blood glucose measurements, hemoglobin A1c values, calorie consumption, exercise activity, weight, height, age, sex, socio-economic status) and derivative data therefrom can be recorded in a storage unit 1220 (e.g., a RAM technology, magnetic, or solid state hard disk technology, flash disk technology, or optical disk technology). All or any portion of the archived data can be retrieved from the storage unit 1220 as necessary for any combination of processing by the analysis unit 1230, presentation to the user by the display/access unit 1250, and transfer to an external device (e.g., for storage, display, or processing) by the communication unit 1240.

The storage unit 1220 can be embedded in one or more storage units, including an EHR system, a picture archiving and communications system (PACS), an OID 100, or any of the sensors in the disease monitoring/management system 1200.

The analysis unit 1230 can be embedded in one or more hardware or software devices, including an EHR system, a picture archiving and communications system (PACS), an OID 100, or any of the sensors in the disease monitoring/management system 1200. The analysis unit 1230 can process any or all of the data or derivative data. In one embodiment, the analysis of data for determining a triggering event (e.g., the risk of diabetic retinopathy) includes any combination of the following: blood flow in the retina, blood vessel density in one or more ROIs of the retina, blood vessel diameter in the retina, blood vessel diameter ratios in one or more ROIs of the retina, classification of vessels as arteries or veins, blood glucose measurements, blood pressure, exercise activity, calorie consumption, retinal images, and laboratory test results.

The communication unit 1240 can consist of any telecommunications device or computing platform capable of transmitting data wirelessly or via a wired connection to another computing platform, including a smartphone, pager, laptop or personal computer, fax machine. In some embodiments, the communication unit 1240 is used to transmit data along with derivative data (e.g., information that has been derived from mathematically processing the data), including indices of aggregated data, image overlays, reports generated from some or all of the data, and alarms or other notifications generated based on analysis of the data or derivative data. In some embodiments, the disease monitoring/management system 1200 uses the communication unit 1240 to transmit a message to a patient, caregiver, healthcare provider, or family member. The message can take the form of one or more electronic mail, instant message, short message service (i.e., text messaging), phone call, fax, paging service (i.e., pager), direct mail (i.e., postal service), and personal communication. The message can be tailored to the recipient. For example, if the recipient is a physician or healthcare provider, the message could be to call the patient into the office for an appointment or to call another provider for more information. If the message is for the patient, the message could be to call the provider to set up an appointment or to inform the patient of disease risk (e.g., onset of diabetic retinopathy) or the need to improve certain aspects of their disease management (e.g., improving exercise, diet, or medication compliance). The messages could also be educational in nature (e.g., general information about the disease). The messages could automatically trigger an event in another device (e.g., an EHR or computerized order entry system). This event could be, for example, to set up an appointment for the patient in the hospital scheduling system or to recommend a specific change to the disease management regimen. The message can originate from any device within the disease monitoring/management system 1200, including an OID 100, an EHR, or blood glucose meter.

The display/access unit 1250 can consist of one or more of a combination of hardware and software systems designed to allow a user to access and/or visualize the data or derivative data, including an OID 100, a web-based application/portal, a mobile software application, a stand-alone software application, a software application embedded in an EHR system, or a software application embedded in another device.

FIG. 12B is a schematic of one embodiment that contains an OID 100, a central communication/storage system (e.g., an EHR system or PACS) 1241, a plurality of patient sensors 1210, and a plurality of user access/display devices 1250. In this embodiment, the OID 100 contains one or more image acquisition units 1201 containing one or more imaging sensors for capturing and converting light along the imaging path 135 to an electronic format, one or more storage units 1202 for temporarily or permanently storing said reflected illumination in an electronic format, one or more image analysis units 1203 for processing and analyzing said reflected illumination stored in an electronic format, and one or more communication/data transmission units 1242 for bidirectional communication with the central communication/storage system 1241. In this embodiment, the plurality of patient sensors 1210 consists of one or more blood glucose meters 1211 for measuring daily blood glucose values, one or more behavioral sensors for monitoring exercise activity and calorie consumption, and one or more communication/data transmission units 1244 for bidirectional communication with the central communication/storage system 1241. In this embodiment, the plurality of user access/display devices 1250 consists of one or more web portals or dashboards 1251 accessible through a plurality of computing platforms (e.g., smartphone, table, or laptop), one or more mobile applications 1252 accessible through a plurality of mobile computing platforms (e.g., smartphone or tablet), and one or more communication/data transmission units 1243 for bidirectional communication with the central communication/storage system 1241. In this embodiment, the one or more web portals or dashboards 1251 and one or more mobile applications 1252 allow the user to view multiple patient records and patient-specific data stored on or accessible through the central communication/storage system 1241.

FIGS. 13A, 13B, and 13C illustrate various embodiments for presenting and assessing parameters generated using the OID 100 in accordance with the various embodiments of the subject technology. FIG. 13A presents a graph of data generated using the OID 100. The data can be presented as individual data points 1314, a trending plot 1315, a change in data point values 1317 and 1318, or a combination thereof. The data can be presented as a function of time 1311, where each data point 1314 is plotted sequentially from the first point to 1312 to the last point $t_N$ 1313 in a chronological, reverse chronological, or other ordering system. In one embodiment, the data points 1314 are blood vessel diameter values for a specific blood vessel in the ROI of the retina obtained using an OID 100 with LSCI functionality. In one embodiment, the data points 1314 are blood flow values for a specific blood vessel in the ROI of the retina obtained using an OID 100 with LSCI functionality. In one embodiment, the data points 1314 are blood vessel length values for a specific blood vessel in the ROI of the retina obtained using an OID 100 with reflectance imaging functionality. In one embodiment, the data points 1314 or trend plot 1315 are presented with data points or trend plots of more than one blood vessel or ROI. An algorithm embedded in the OID 100 or the disease monitoring/management system 1200 can analyze a single data point 1314 or the trend 1315 to determine the functional properties of the blood vessel or the retina, or the risk of a disease or condition (e.g., diabetic retinopathy). In one embodiment, interpolation is used to estimate missing data points and extrapolation based on trends is used to estimate data points not yet obtained. In the same or another embodiment, curve fitting approaches are used to find and address (to prevent discarding) seemingly aberrant data points. In another embodiment, the algorithm uses a threshold 1316 to determine whether the value of a data point 1314 suggests, for example, an increased risk for a disease or condition (e.g., diabetic retinopathy). In another embodiment, the algorithm uses the change in data point values between two consecutive points to determine whether a threshold has been crossed. For example, the slope of lines 1317 and 1318 can be compared to the slope of line 1319, which acts as the slope threshold for determining the significance of the change in the data points. The slope of lines 1317 and 1318 can be compared to each other to determine the significance of the change. Thresholds 1316 and 1319 can be pre-determined based on the individual patient, a patient population dataset, or some other benchmark. Thresholds 1316 and 1319 can be adjusted automatically or manually. FIG. 13B represents the use of multiple thresholds to, for example, characterize the degree of conformance of the data to a set standard. In this embodiment, certain data points fall within a region of high conformance 1326, while others fall within a region of moderate conformance 1327, and yet others fall within a region of low conformance 1328. As with thresholds 1316 and 1319, these regions of conformance 1326, 1327, and 1328 can be pre-determined based on the individual patient, a patient population dataset, or some other benchmark and can be adjusted automatically or manually. FIG. 13C represents the use of multiple thresholds to, for example, stratify risk levels. In this embodiment, certain data points fall within the lowest risk level 1336, while others fall within a moderate risk level 1337, and yet others fall within a high risk level 1338. As with thresholds 1316 and 1319, these risk levels 1336, 1337, and 1338 can be pre-determined based on the individual patient, a patient population dataset, or some other benchmark and can be adjusted automatically or manually.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

A phrase such as "an aspect" does not imply that such aspect is essential to the subject technology or that such aspect applies to all configurations of the subject technology. A disclosure relating to an aspect may apply to all configurations, or one or more configurations. An aspect may provide one or more examples of the disclosure. A phrase such as "an aspect" may refer to one or more aspects and vice versa. A phrase such as "an embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples of the disclosure. A phrase such "an embodiment" may refer to one or more embodiments and vice versa. A phrase such as "a configuration" does not imply that such configuration is essential to the subject technology or that such configuration applies to all configurations of the subject technology. A disclosure relating to a configuration may apply to all configurations, or one or more configurations. A configuration may provide one or more examples of the disclosure. A phrase such as "a configuration" may refer to one or more configurations and vice versa.

As used herein, the phrase "at least one of" preceding a series of items, with the terms "and" or "or" to separate any of the items, modifies the list as a whole, rather than each member of the list (i.e., each item). The phrase "at least one of" does not require selection of at least one item; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Terms such as "top," "bottom," "front," "back" and the like as used in this disclosure should be understood as referring to an arbitrary frame of reference, rather than to the ordinary gravitational frame of reference. Thus, a top surface, a bottom surface, a front surface, and a back surface may extend upwardly, downwardly, diagonally, or horizontally in a gravitational frame of reference.

Furthermore, to the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

As used herein, the term "real time" shall be understood to mean the instantaneous moment of an event or condition, or the instantaneous moment of an event or condition plus short period of elapsed time used to make relevant measurements, optional computations, etc., and communicate the measurement, computation, or etc., wherein the state of an event or condition being measured is substantially the same as that of the instantaneous moment irrespective of the elapsed time interval. Used in this context "substantially the same" shall be understood to mean that the data for the event or condition remains useful for the purpose for which it is being gathered after the elapsed time period.

A reference to an element in the singular is not intended to mean "one and only one" unless specifically stated, but rather "one or more." Pronouns in the masculine (e.g., his) include the feminine and neuter gender (e.g., her and its) and vice versa. The term "some" refers to one or more. Underlined and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While certain aspects and embodiments of the invention have been described, these have been presented by way of example only, and are not intended to limit the scope of the invention. Indeed, the novel methods and systems described herein may be embodied in a variety of other forms without departing from the spirit thereof. The accompanying claims and their equivalents are intended to cover such forms or modifications as would fall within the scope and spirit of the invention.

What is claimed is:

1. A disease management system, comprising:
an ophthalmic imaging device including:
  an illumination module capable of generating coherent light;
  a first optical assembly configured to direct the coherent light to a region of interest of a fundus of an eye;
  an imaging sensor configured to generate image data based on light received from the region of interest; and
  a second optical assembly configured to direct the light from the region of interest to the imaging sensor; and
one or more processors configured to:
  calculate laser speckle contrast values based on the image data;
  receive first patient-specific data generated using one or more sensors, the one or more sensors including one or more of a blood glucose meter, a continuous glucose monitor, an infusion pump, a weight scale, or an exercise sensor; and
  generate, based on the laser speckle contrast values and the first patient-specific data, first data for display on a display device, the first data representing the first patient-specific data and a laser speckle contrast image indicative of blood flow in the region of interest.

2. The disease management system of claim 1, wherein the one or more processors are further configured to:
analyze the laser speckle contrast values to determine blood vessel information including one or more of blood flow, blood vessel density, blood vessel diameter, or classification of vessels as arteries or veins.

3. The disease management system of claim 2, wherein the one or more processors are further configured to:
generate, based on the blood vessel information, second data for display on a display device, the second data including a graph of the blood vessel information presented as a function of time.

4. The disease management system of claim 2, wherein the one or more processors are further configured to:
analyze the blood vessel information and the first patient-specific data to determine an increased risk of diabetic retinopathy.

5. The disease management system of claim 4, wherein the one or more processors are further configured to:
determine the increased risk of diabetic retinopathy based on a trend in the blood vessel information as a function of time.

6. The disease management system of claim 4, wherein the one or more processors are further configured to:
determine a level of increased risk of diabetic retinopathy based on the blood vessel information.

7. The disease management system of claim 1, wherein the first optical assembly and the second optical assembly share at least a first optical element.

8. The disease management system of claim 1, wherein the ophthalmic imaging device further includes:
a second illumination module capable of generating incoherent light,
  wherein the one or more processors are further configured to generate, based on the image data, second data for display on a display device, the second data representing one or more of a reflectance image, spectroscopic image, or fluorescence image.

9. The disease management system of claim 1, wherein:
the first patient-specific data further includes one or more of second patient-specific data from an electronic journal, electronic health record, laboratory information system, or generated using a food consumption sensor; and
the one or more processors are further configured to generate the first data based additionally on the second patient-specific data.

10. A method comprising:
illuminating a region of interest of a fundus of an eye with coherent light;
receiving light from the region of interest;
generating image data based on the light;
calculating laser speckle contrast values based on the image data;
receiving first patient-specific data generated using one or more sensors, the one or more sensors including one or more of a blood glucose meter, a continuous glucose monitor, an infusion pump, a weight scale, or an exercise sensor; and
generating, based on the laser speckle contrast values and the first patient-specific data, first data for display on a display device, the first data representing the first patient-specific data and a laser speckle contrast image indicative of blood flow in the region of interest.

11. The method of claim 10, further comprising:
analyzing the laser speckle contrast values to determine blood vessel information including one or more of blood flow, blood vessel density, blood vessel diameter, or classification of vessels as arteries or veins.

12. The method of claim 11, further comprising:
generating, based on the blood vessel information, second data for display on a display device, the second data including a graph of the blood vessel information presented as a function of time.

13. The method of claim 11, further comprising:
analyzing the blood vessel information and the first patient-specific data to determine an increased risk of diabetic retinopathy.

14. The method of claim 13, wherein the eye is the eye of a patient, further comprising:
generating, based on the increased risk, a notification indicative of the increased risk; and
sending the notification to a device associated with the patient and/or a caregiver of the patient.

15. The method of claim 13, further comprising:
determining the increased risk of diabetic retinopathy based on a trend in the blood vessel information as a function of time.

16. The method of claim 13, further comprising:
determining a level of increased risk of diabetic retinopathy based on the blood vessel information.

17. The method of claim 10, further comprising:
generating incoherent light; and
generating, based on the image data, second data for display on a display device, the second data representing one or more of a reflectance image, spectroscopic image, or fluorescence image.

18. The method of claim 10, wherein:
the first patient-specific data further includes one or more of second patient-specific data from an electronic journal, electronic health record, laboratory information system, or generated using a food consumption sensor; and
generating the first data is based additionally on the second patient-specific data.

* * * * *